US007175981B2

(12) United States Patent
Jett et al.

(10) Patent No.: US 7,175,981 B2
(45) Date of Patent: Feb. 13, 2007

(54) METHOD OF DIAGNOSING STAGE OR AGGRESSIVENESS OF BREAST AND PROSTATE CANCER BASED ON LEVELS OF FATTY ACID BINDING PROTEINS

(75) Inventors: Marti Jett, Washington, DC (US); Rina Das, Rockville, MD (US); Roger Neill, Rockville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/451,513

(22) Filed: Nov. 30, 1999

(65) Prior Publication Data
US 2002/0127619 A1 Sep. 12, 2002

Related U.S. Application Data

(60) Provisional application No. 60/110,484, filed on Dec. 1, 1998.

(51) Int. Cl.
*C12Q 1/68* (2006.01)
*G01N 33/53* (2006.01)
*G01N 33/567* (2006.01)
*G01N 33/48* (2006.01)

(52) U.S. Cl. .................. 435/6; 435/7.1; 435/7.2; 435/7.21; 435/7.23; 436/63; 436/64

(58) Field of Classification Search .............. 530/350, 530/359; 514/21; 435/91.2, 7.1, 7.23, 6, 435/7.21; 436/63, 64
See application file for complete search history.

(56) References Cited

U.S. PATENT DOCUMENTS 4,547,369 A   10/1985   Chermann et al. .......... 424/131

OTHER PUBLICATIONS

Carroll et al., Gastroenterology vol. 99, No. 6, pp. 1727-1735, Dec. 1990.*
Huynh et al., Cancer Research, vol. 56, pp. 4865-4870, Sep. 1996.*
DeVita et al., Cancer: Principles and Practice of Oncology, 6th Edition, Section 4, pp. 1418-1479, 2001.*
Alberts et al., Molecular Biology of the Cell, 3rd Edition, 1994, p. 465.*
Shantz and Pegg, International Journal of Biochemistry and Cell Biology, 1999, vol. 31, pp. 107-122.*
McClean and Hill, European Journal of Cancer, 1993, vol. 29A, pp. 2243-2248.*
Fu et al., EMBO Journal, 1996, vol. 15, pp. 4392-4401.*
Khan SH and Sorof S.: Liver fatty acid-binding protein: specific mediator of the mitogenesis induced by two classes of carcinogenic peroxisome proliferators., Proc. Natl. Acad. Sci. USA 91:848-52 (1994).
Celis, et al., Loss of adipocyte-type fatty acid binding protein and other protein biomarkers is associated with progression of human bladder transitional cell carcinomas, Cancer Res 56;4782-90 (1996).
Ostergaard, et al., Proteome profiling of bladder squamous cell carcinomas: identification of markers that define their degree of differentiotion., Cancer Res 57:4111-7 (1997).
Specht, et al., Mammary Derived Growth Inhibitor is not a Distinct Protein but a Mix of Heart-type and Adipocyte-type Fatty Acid-binding Protein, The Journal of Biological Chemistry, vol. 271, No. 33, 19943-19949 (1996).
Chaudry, et al., Purification and characterization of a fatty acid binding protein from human prostatic tissue, Lipids 28: 383-8 (1993).
Borchers, et al, Heart-type fatty acid binding protein-involvement in growth inhibition and differentiation, Prostaglandins, Leukotrienes and Essential Fatty Acids, 57(1), p. 77-84 (1997).
Biological Abstracts, Philadelphia, PA US,; abstract No. PREV199900172126, R. Das et al., "Expression pattern of different fatty acid binding proteins in breast cancer cells", Proceedings of the Americal Association for Cancer Research Annual Meeting,(Mar. 1, 1999) vol. 40, p. 363.
Medline, Washiington DC USA, abstract No. 96438639, J.E. Celis et al, "Loss of adipocyte-type fatty acid binding protein and other protein biomarkers is associated with progression of human bladder transitional cell carcinomas", Cancer Research, vol. 56, No. 20, Oct. 15, 1996.
Biological Abstracts, Philadelphia PA USA, abstract No. PREV199699030662, Y. Wang ety al., Heteropolyanions do not induce P-glycoprotein associated with multidrug resistance inhuman breast cancer cells, FASEB Journal, vol. 10, No. 6, Jun. 2, 1996, p. a1145.
Medline, Washington DC USA, abstract No. 98314895, M. Thullberg et al., "changes in liver fatty acid-binding protein in rat enzyme-altered foci", Cancer Letters, vol. 128, No. 1, Jun. 5, 1998, pp. 1-10.

* cited by examiner

*Primary Examiner*—Larry R. Helms
*Assistant Examiner*—Anne L. Holleran
(74) *Attorney, Agent, or Firm*—Elizabeth Arwine; Charles H. Harris

(57) ABSTRACT

A method of diagnosing the stage or aggressiveness of cancer and particularly breast and prostate cancer by measuring the deviation of levels of fatty acid binding proteins in mammalian tissue or body fluids from normal levels of fatty acid binding proteins. The invention relates to a family of key proteins called fatty acid binding proteins which are involved in metabolism of AA and other lipids and how they affect the proliferation of cancer cells.

11 Claims, 22 Drawing Sheets

FIG. 3
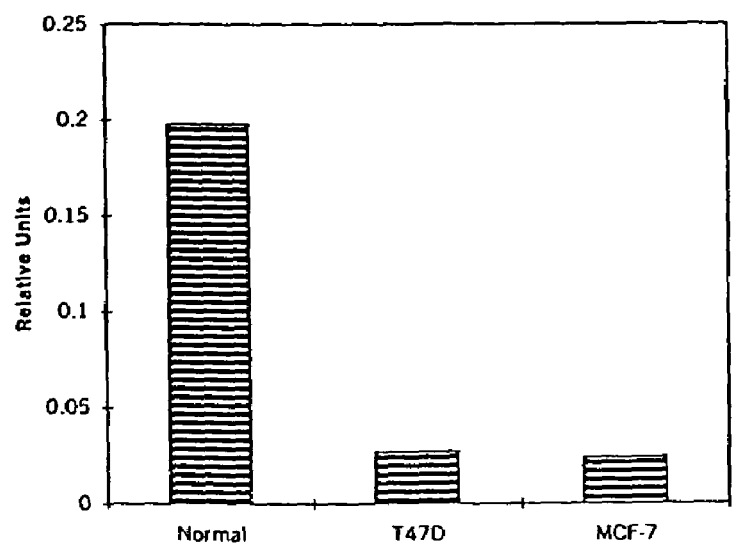
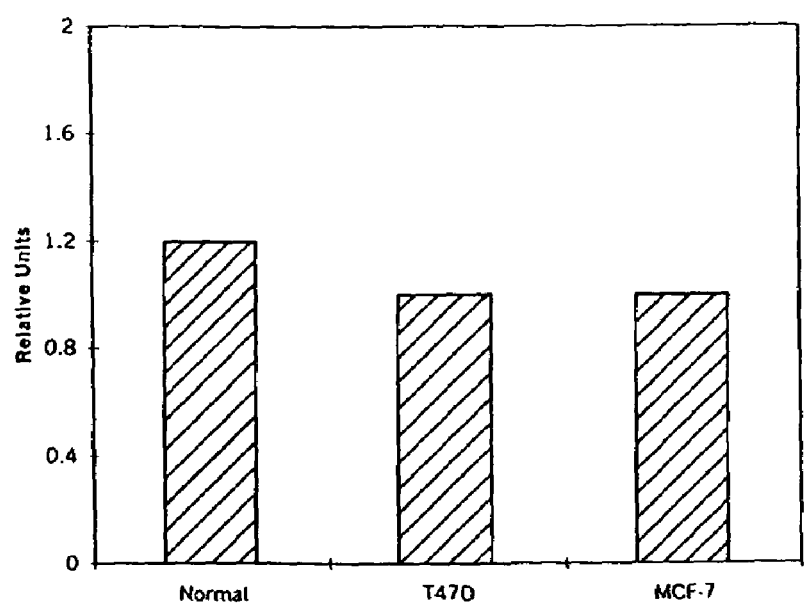
FIG. 4

Cells were synchronized by thymidine block for 12 h. At that time the cells were washed x2 and fresh culture fluid alone or containing the indicated drugs were added. For each of the drugs, cells became apoptotic by 28 h and the percentage increased through 36 h.

us 7,175,981 b2

METHOD OF DIAGNOSING STAGE OR AGGRESSIVENESS OF BREAST AND PROSTATE CANCER BASED ON LEVELS OF FATTY ACID BINDING PROTEINS

This application claims priority of Provisional Application Ser. No. 60/110,484 filed Dec. 1, 1998.

FIELD OF THE INVENTION

The present invention relates to a novel method of diagnosing the stage or aggressiveness of cancer and particularly breast and prostate cancer. The diagnosis is made based on deviations in measured levels of fatty acid binding proteins in mammalian tissue or body fluids from normal levels of fatty acid binding proteins. The present invention further relates to novel compositions, and uses thereof, for treating breast and prostate cancer.

BACKGROUND OF THE INVENTION

Although screening mammography and the increased use of breast conserving surgery and adjuvant chemotherapy have improved the quality of life and prolonged survival for women with breast cancer, additional therapeutic strategies are needed to combat the disease. Various studies have suggested dietary fat, especially polyunsaturated fatty acids, promotes tumor growth by increasing synthesis of eicosanoids, particularly arachidonic acid (AA) products. The possible role of AA-derived eicosanoids as regulators of neoplastic cell growth is an area of significant interest in breast cancer biology.

Digital Rectal Examination (DRE) and Prostate Specific Antigen (PSA) tests are routinely used to screen for the presence of prostate cancer in men. However, there is a serious debate in the medical community as to whether DRE and/or PSA screening accurately predict the presence of prostate cancer. For instance, the American Cancer Society now recommends that physicians inform men screened for prostate cancer that a PSA result of less than 4.0 ng/ml does not guarantee that cancer is not present, because up to 25% of men with the disease can have PSA levels of under 4.0 ng/ml. Furthermore, an "abnormal" or elevated PSA can be caused by benign growth, inflammation, or other causes. Therefore, a number of men with elevated PSA levels may require additional diagnostic tests and in the end, some may not require treatment.

Epidemiological studies on carcinoma of the prostate gland have shown a positive relationship between the consumption of dietary fats and development of prostate cancer. (Franceschi S.: Fat and prostate cancer. Epidemiol 5:271–273, 1994.; Snowdon D A, Phillips R L and Choi W.: Diet obesity and risk of fatal prostatic cancer. Amer J Epidemiol 2:244–250, 1984). This led to the suggestion that high dietary fat intake may be a contributing factor in the initiation or development of this tumor (Wynder E L, Laakso K, Sotarauta M and Rose D.: Metabolic epidemiology of prostatic cancer. Prostate 5:47–53, 1984). Conversely, (Wang U, Corr J G, Thaler H T, Tao Y, Fair W R and Heston W D W.: Decreased growth of established human prostate LNCaP tumors in nude mice fed a low-fat diet. J. Nat Cancer Inst 87:1456–1462, 1995) showed that lowering the quantity of fat as a proportion of total calories decreased the growth rate of human prostate adenocarcinoma cells in mice.

Studies have implicated an association of linoleic acid (LA), a constituent of dietary fat, with prostate cancer. Linoleic acid is the most prevalent unsaturated fatty acid component of commonly used cooking oils. A large prospective study of American men showed a positive association between linoleic acid in the diet and prostate cancer. (Giovannucci E, Rimm E B, Colditz G A, Stampfer M J, Ascherio A, Chute C C and Willett W C.: A prospective study of dietary fat and risk of prostate cancer. J Nat Cancer Inst 85:1571–1579, 1993). Moreover, in vitro studies of the human prostate cancer cell line PC-3 showed stimulated growth in the presence of linoleic acid whereas the long chain fatty acids may inhibit tumorigenesis. (Rose DP and Connolly J M.: Effects of fatty acids and eiconsanoid synthesis inhibitors on the growth of two human prostate cancer cell lines. Prostate 1811243–254:1991). Recently Harvei et al. showed an association of serum levels of linoleic acid and palmitic acid with increased risk of prostate cancer. (Harvei S, Bjerve K S, Tretli S, Jellum E, Robsahm T E and Vatten L.: Prediagnostic level of fatty acids in serum phospholipids: $\Omega$-3 and $\Omega$-6 fatty acids and the risk of prostate cancer. Int J Cancer 71:545–551, 1997).

There are no current serum tests available for breast cancer. The present screening tests for breast and prostate cancer do not take into account the presence of fats or fat-metabolizing substances in body tissue or fluids. There exists a need for improved methods of diagnosing and treating cancer, particularly breast and prostate cancer. There further exists a need for a composition of matter for use in the treatment of cancer, particularly breast and prostate cancer.

It has been shown that there is a positive correlation between high dietary fat and development of breast cancer. Thus, it appears that arachidonic acid acts as a potent mitogen for human breast cancer cells. FABPs bind fatty acids noncovalently with high affinity and translocates them across the cell to the nuclear receptors. The existence of various FABP types and the relative abundance of these cytoplasmic proteins in nearly all tissues indicate important functions for these molecules.

AA and its metabolites are well known to bind to the FABP with high affinity in liver carcinogenesis. The expression of one of the FABPs, designated L-FABP, has been shown to be upregulated in liver during carcinogenesis. (Custer R P and Sorof S.: Target polypeptide of a carcinogen is associated with normal mitosis and carcinogen-induced hyperplasias in adult hepatocytes. Proc Natl Acad Sci USA 81:7638–6742, 1984. Custer R P and Sorof S.: Mitosis in hepatocytes is generally associated with elevated levels of the target polypeptide of a liver carcinogen. Differentiation 30:176–181, 1985). Furthermore, secreted L-FABP has been detected in serum of rats with hepatocarcinoma. Only one previous study addressed the issue of FABPs in prostate cancer (Chaudry A A and Dutta-Roy A K.: Purification and characterization of a fatty acid binding protein from human prostatic tissue. Lipids 28:383–8, 1993.). That study suggested that an L-FABP-like protein occurred in both normal and cancerous prostate cells. Other FABP types have never been identified in prostate gland and have never been implicated in control of cell proliferation or cancer. The levels of L-FABP has been shown to increase in liver carcinogenesis compared to the normal tissue and L-FABP is also known to be secreted in the serum, however nothing is known about the levels of FABPs in different stages of breast cancer, or the effect of hormones, growth factors or bioactive lipids on FABPs.

Certain FABPs have been reported to have differential effects on cell growth when cDNA clones have been transfected into these cells. Transfection of L-FABP into hepatoma cells increased proliferation (Keler T, Barker C S and Sorof S.: Specific growth stimulation by linoleic acid in hepatoma cell lines transfected with the target protein of a liver carcinogen. Proc Natl Acad Sci USA 89:4830–4, 1992; Keler T and Sorof S.: Growth promotion of transfected hepatoma cells by liver fatty acid binding protein. J Cell Physiol 157:33–40, 1993; Sorof S.: Modulation of mitogenesis by liver fatty acid binding protein. Cancer Metastasis Rev 13:317–36, 1994.). In contrast, MDGI (H-FABP) appears only in normal and not tumor mammary cells (Grosse R, Boehmer F D, Langen P, Kurtz A, Lehmann W, Mieth M and Wallukat G.: Purification, biological assay and immunoassay of mammary-derived growth inhibitor. Methods Enzymol 198:425–440, 1991; Grosse R and Langen P.: Mammary derived growth inhibitor. In M. Sporn and A. Roberts, eds Handbook of Experimental Pharmacology. Heidelberg, 1990, pp 249–265.) and transfection of a cDNA clone of MDGI into breast cancer cells or mouse mammary epithelial cells results in loss of tumorigenicity (Huynh H, Alpert L and Pollak M.: Silencing of the mammary-derived growth inhibitor (MDGI) gene in breast neoplasms is associated with epigenetic changes. Cancer Res 56:4865–70, 1996.). FABPs are known to bind many different groups of fatty acids and their derivatives, including eicosanoids and other bioactive lipids, reviewed in (Veerkamp J H, Peeeters R A and Matman R G H J.: Structural and functional features of different types of cytoplasmic fatty acid-binding proteins. Biochim Biophys Acta 1081:1–24, 1991). L-FABP exhibits different lipid binding characteristics from that of A-FABP or H-FABP. L-FABP transfected into rat hepatoma cells also mediates cell induction by carcinogenic peroxisome proliferators (Khan S H and Sorof S.: Liver fatty acid-binding protein: specific mediator of the mitogenesis induced by two classes of carcinogenic peroxisome proliferators. Proc Natl Acad Sci U S A 91:848–52, 1994.). Several studies suggest that FABP increases the solubility of fatty acids in the cell cytoplasm causing a net diffusion of fatty acids from the plasma membrane to the intracellular membrane compartments (Tipping E and Ketterer B.: The influence of soluble binding proteins on lipophile transport and metabolism in hepatocytes. Biochem J 195:441–52, 1981; Vork M M, Glatz J F C and Van Der Vusse G J.: On the mechanism of long chain fatty acid transport in cardiomyocytes as facilitated by cytoplasmic fatty acid-binding protein. J Theoret Biol 160: 207–222, 1993.).

L-FABP is elevated significantly in metastatic or regenerating liver vs normal liver. This is in stark contrast to H-FABP, also known as mammary derived growth inhibitor (MDGI). It is present only in normal lactating breast, and completely disappears in mammary cancer cells (Grosse R, Boehmer F D, Langen P, Kurtz A, Lehmann W, Mieth M and Wallukat G.: Purification, biological assay and immunoassay of mammary-derived growth inhibitor. Methods Enzymol 198:425–440, 1991; Grosse R and Langen P.: Mammary derived growth inhibitor. In M. Sporn and A. Roberts, eds Handbook of Experimental Pharmacology. Heidelberg, 1990, pp 249–265). The inventors were intrigued by the differences in the effects on proliferation of MDGI vs L-FABP. The inventors performed a similar study (to the eicosanoid generation in hepatic cells) in MCF-7 cells transfected with a clone of the MDGI (H-FABP) gene or vector alone. The inventors also have examined these pairs of cells to determine cell cycle pattern changes related to MDGI (You Y., Zhang X., Das R. and Jett M. (1997) Cell cycle effects of mammary derived growth inhibitor in MDGI gene transfected breast cancer cells. In 37th Annual Meeting of American Society for Cell Biology, Abst #88.).

Changes in expression of FABPs have been reported for bladder cancer. Psoriasis-associated FABP (E-FABP) was noted to increase in level with increase in differentiation of bladder squamous cell carcinomas (Ostergaard M, Rasmussen H H, Nielsen H V, Vorum H, Orntoft T F, Wolf H and Celis J E.: Proteome profiling of bladder squamous cell carcinomas: identification of markers that define their degree of differentiation. Cancer Res 57:4111–7, 1997.). Although FABPs are intracellular proteins, H-FABP has been detected in elevated levels in plasma and urine of patients suffering from myocardial infarction, (Sohmiya K, Tanaka T, Tsuji R, Yoshimoto K, Nakayama Y, Hirota Y, Kawamura K, Matsunaga Y, Nishimura S and Miyazaki H.: Plasma and urinary heart-type cytoplasmic fatty acid-binding protein in coronary occlusion and reperfusion induced myocardial injury model. J Mol Cell Cardiol 25:1413–26, 1993; Van Nieuwenhoven F A, Kleine A H, Wodzig W H, Hermens W T, Kragten H A, Maessen J G, Punt C D, Van Dieijen M P, Van der Vusse G J and Glatz J F.: Discrimination between myocardial and skeletal muscle injury by assessment of the plasma ratio of myoglobin over fatty acid-binding protein. Circulation 92:2848–54, 1995; Wodzig K W, Kragten J A, Hermens W T, Glatz J F and van Dieijen-Visser M P.: Estimation of myocardial infarct size from plasma myoglobin or fatty acid-binding protein. Influence of renal function. Eur J Clin Chem Clin Biochem 35:191–8, 1997.) whereas psoriasis-associated FABP (E-FABP) was among a number of marker proteins detected in the urine of bladder cancer patients (Rasmussen H H, Orntoft T F, Wolf H and Celis J E.: Towards a comprehensive database of proteins from the urine of patients with bladder cancer. J Urol 155:2113–9, 1996.). In addition, loss of adipocyte-FABP (A-FABP) was reported with progression of human bladder transitional cell carcinomas (Celis J E, Ostergaard M, Basse B, Celis A, Lauridsen J B, Ratz G P, Andersen I, Hein B, Wolf H, Orntoft T F and Rasmussen H H.: Loss of adipocyte-type fatty acid binding protein and other protein biomarkers is associated with progression of human bladder transitional cell carcinomas. Cancer Res 56:4782–90, 1996.). The presence of A-FABP correlated with the grade and stage of the disease. The A-FABP protein was present in high levels in grade I and II TCCs whereas grade III had 37% reduction and grade IV had no A-FABP expression. A-FABP may act as a growth inhibitor similar to the MDGI (H-FABP) protein in breast cancer and loss of A-FABP expression may serve as a prognostic marker for aggressive bladder cancer.

Although FABPs are intracellular proteins, H-FABP has been detected in elevated levels in plasma and urine of patients suffering from myocardial infarction (Sohmiya K, Tanaka T, Tsuji R, Yoshimoto K, Nakayama Y, Hirota Y, Kawamura K, Matsunaga Y, Nishimura S and Miyazaki H.: Plasma and urinary heart-type cytoplasmic fatty acid-binding protein in coronary occlusion and reperfusion induced myocardial injury model. J Mol Cell Cardiol 25:1413–26, 1993; Van Nieuwenhoven F A, Kleine A H, Wodzig W H, Hermens W T, Kragten H A, Maessen J G, Punt C D, Van Dieijen M P, Van der Vusse G J and Glatz J F.: Discrimination between myocardial and skeletal muscle injury by assessment of the plasma ratio of myoglobin over fatty acid-binding protein. Circulation 92:2848–54, 1995; Wodzig K W, Kragten J A, Hermens W T, Glatz J F and van Dieijen-Visser M P.: Estimation of myocardial infarct size from plasma myoglobin or fatty acid-binding protein. Influence of renal function. Eur J Clin Chem Clin Biochem 35:191–8, 1997), whereas psoriasis-associated FABP (E-FABP) was among a number of marker proteins detected in the urine of bladder cancer patients (Rasmussen H H, Orntoft T F, Wolf H and Celis J E.: Towards a comprehensive database of proteins from the urine of patients with bladder cancer. J Urol 155:2113–9, 1996.). In addition, loss of adipocyte-FABP (A-FABP) was reported with progression of human bladder transitional cell carcinomas (Celis J E, Ostergaard M, Basse B, Celis A, Lauridsen J B, Ratz G P, Andersen I, Hein B, Wolf H, Orntoft T F and Rasmussen H H.: Loss of adipocyte-type fatty acid binding protein and other protein biomarkers is associated with progression of human bladder transitional cell carcinomas. Cancer Res 56:4782–90, 1996). The presence of A-FABP correlated with the grade and stage of the disease.

These results suggests that A-FABP and E-FABP may act as a tumor suppressors in prostate cells similar to MDGI (H-FABP) in MCF-7 cells (Huynh H, Alpert L and Pollak M.: Silencing of the mammary-derived growth inhibitor (MDGI) gene in breast neoplasms is associated with epigenetic changes. Cancer Res 56:4865–70, 1996.). Of the few FABPs tested so far, the inventors have found altered levels of FABPs; individually, each of these have been shown, in other cell systems, but not in breast or prostate to correlate with the normal or tumor state. The inventors are the first to show concomitant decreases in the heart-type FABPs (A-, H- and E-FABPs) and increases in mitosis promoting FABPs (I-, B- and L-FABP). These data support the notion that level(s) of FABP(s) will correlate with stage of prostate cell proliferation and perhaps aggressive tumors.

The inventors have shown for the first time the presence of multiple FABPs in different tissue types of cancer and have shown that the levels of the different FABPs are indicative of the presence and stage of cancer. For instance, the FABP message (L- and I-FABP) can be even 22 fold higher in tumor vs normal breast cells, especially in the estrogen receptor positive lines. The inventors have also discovered that the A-FABP, E-FABP class of proteins are downregulated in breast cancer cells. Prior to this study by the inventors, it has never been shown or suggested that the pattern of multiple forms of FABP play a significant role in carcinogenesis or that the presence of cancer can be diagnosed by measuring the level and types of FABPs present in a biopsy sample or serum sample.

The inventors have also discovered that free-radical scavengers called heteropolyanions (HPA), can effectively block the proliferation in cultures of breast tumor cells. Although HPAs were previously known, they were used for the treatment of HIV. The inventors have synthesized and identified free-radical scavengers, heteropolyanions, which effectively blocked proliferation in cultures of breast tumor cells. Prior to the inventors, no one had shown the effect of HPA on the growth of these breast cancer cells and the changes in the levels of these FAPB that play a role in carcinogenesis. No one has ever suggested treating cancer with an HPA or that HPA can affect the growth of breast or prostate cancer cells. Thus, FABPs also present a logical target for such intervention therapeutic drugs, which interrupt their crucial function of transmitting the cascades of signals of bioactive lipids that continually promote cancer cell proliferation.

The inventors have provided a basis for a better understanding of the direct role of fatty acids/bioactive lipids and FABPs in development and progression of breast cancer. FABPs can also be used as potential marker for breast cancer or, more specifically, for an aggressively growing breast cancer. There are no known detection markers for identification of breast cancer in a patient. The present invention can operate as a screening test for breast cancer.

It is therefore, an object of the present invention to provide a reliable method of diagnosing stage or aggressiveness of cancer, particularly breast and prostate cancer by measuring the presence and amounts of certain types of FABPs.

It is also an object of the present invention to provide a composition containing HPA in the form of a drug for treating cancer to block the cancer initiating function of certain FABPs.

These and other objects of the invention will become apparent from the following description.

SUMMARY OF THE INVENTION

The invention relates to methods of diagnosing and treating tissue or organ cancer, particularly breast and prostate cancer. The invention also relates to diagnosing and treating liver cancer, lung cancer, brain cancer, kidney cancer, pancreatic cancer, colon cancer and ovarian cancer. The invention also describes the use of compositions to treat breast and prostate cancer. Specifically, the invention focuses on the role of a family of key proteins involved in metabolism of AA and other lipids. The inventors have found that these proteins, called fatty acid binding proteins (FABP), are useful in (a) screening body fluids (the FABPs are known to be secreted) as indicators of cancer, (b) assessing biopsy samples for indicators of stage characteristics and metastatic disease, and (c) as therapeutic targets.

The inventors suggest that some of the FABP's actually increase the proliferation of cancer cells while others decrease the proliferation of cancer cells, while still others seem to have no apparent affect on the presence of cancer cells.

Breast Cancer:

In breast cancer, AA, a key fatty acid, has far-reaching biological effects by producing cascades of biologically potent metabolites. Because of this, AA and its metabolites are among the molecules referred to as bioactive lipids. The method by which AA and other bioactive lipids causes its biological effects involves a family of proteins within cells called fatty acid binding proteins (FABPs).

FABPs are named according to their original site of discovery, although most types have been found to occur in numerous different organs/tissues. Liver-FABP has been associated, in hepatic cells with increased cell proliferation (carcinogenesis or liver regeneration). In contrast, a FABP from the mammary gland, mammary derived growth inhibitor (MDGI) was singularly absent in cancer cells, appearing only during lactation. As such, MDGI has been regarded as being associated with the "normal" lactating breast (a) because of this absence in breast cancer cells/tissues and (b) when it is added exogenously, MDGI blocks the growth of breast cancer cells in vitro. The inventors suggest that the role of MDGI, in that specialized state, is to protect the epithelial cells from the incredibly rich mileu of bioactive lipids and other factors that bath the cells during lactation. Therefore, the inventors realized that other FABPs play a role in normal/tumor breast cells and the inventors now have data implicating the presence of several different FABPs in breast cells and an altered balance of several FABPs between normal and tumor breast cells.

The inventors have found liver (L)-FABP and intestine (I)-FABP to be significantly elevated (22- and 3-fold, respectively) in breast tumor vs normal cells. Meanwhile, the inventors found the reverse to be true in the case of adipose (A)-FABP and epidermal E-FABP which was 7-fold less in tumor cells than in normal cells. These proteins bind to bioactive lipids, including AA. In liver, prior art suggests that the FABP transports bioactive lipids to the nuclear membrane to receptors which initiate the uncontrolled growth typical of cancer. The inventors have found that this, coupled with the incredible increases in bioactive lipids in breast tumors, suggests that bioactive lipid utilization is critical for a) understanding the progression of the disease, identification of potential markers of aggressive and perhaps, metastasizing, tumors and b) also presents a logical therapeutic target for development of specific drugs.

The inventors have characterized for the first time the FABPs in tumor vs normal breast cells in terms of the activity and type of FABP(s) elevated in tumor cells. In, addition, the inventors expect that elevated FABPs may be secreted into bodily fluids in sufficient amounts for detection. For example, we have demonstrated in prostate cancer cells, that L-FABP was secreted into the culture fluid but normal prostate cells did not secrete measurable amounts of this protein. In addition, previous studies have shown that a) H-FABP was secreted into plasma during severe myocardial infarction and b) E-FABP was decreased in urine in bladder cancer. The inventors have shown that the pattern of B-, L-, I-FABPs, taken together, along with decreases in A-, E-, and H-FABPs, are indicative of the relative agressiveness of the cancer. The pattern of FABPs provide potential markers to help patients choose a treatment modality. Also, treatment aimed at breast FABPs and bioactive lipid utilization presents a logical target for therapy.

Prostate Cancer:

High dietary fat has also been shown to play a major role in prostate cancer. Arachidonic acid (AA) has been shown to be elevated 10-fold in prostate tumor vs normal tissue. It acts as a potent mitogen for human prostate cancer cells, especially the 5-HETE series of its metabolites. Utilization of AA and other bioactive lipids occurs through fatty acid binding proteins (FABPs) which bind to bioactive lipids in the cell cytoplasm. This causes a net diffusion of fatty acids from the plasma membrane to the intracellular membrane compartments. FABPs then deliver eicosanoids and other bioactive lipids to nuclear receptors such as peroxisome proliferator-activated activated receptor (PPAR) or retinoic X receptor (RXR). Using RT-PCR primer pairs designed to identify different FABPs, the inventors have identified 3 tumor-associated FABPs that were elevated in tumor vs normal prostate cells from 5–100 fold and in breast cells from 3–18 fold. Furthermore, the normal cell-associated FABPs (E-, A-, and H-FABPs) were decreased in tumor cells (3–11 fold). In patient specimens of normal and tumor prostate tissue, these patterns were repeated, in some cases to an even greater degree (FIG. 10).

The inventors have established a battery of PCR primer pairs by methods well known in the art that are directed toward different types of FABPs and have correlated the levels of FABP with various stages of prostate cancer compared to normal prostate cells. This was initially examined using established human prostate cell lines exemplifying different progressive stages of prostate cancer (adenoma, carcinoma, and metastatic stages). The evidence indicates that the levels of bound eicosanoids to these FABPs are different in prostate cancer cells compared to the normal cells. These findings have been confirmed by screening of human prostate cancer/normal biopsy samples.

The inventors have found that a series of drugs, heteropolyanion free radical scavengers act as cancer inhibitors target the intracellular activities of the FABPs effectively (at very low concentrations). They effectively modulate the intracellular levels of the FABPs and essentially cause the cells to revert from the FABP pattern typical of tumor cells to the FABP pattern characteristic of normal cells. Consequently, these drugs lead to a decrease in breast or prostate tumor cell proliferation.

The HPA drugs increased the levels of the "normal cell-associated" FABPs (A-, E-, H-) and decrease the level of the "tumor-associated" FABPs (L-, I-, B-); this ultimately blocked prostate tumor cell proliferation. These HPA drugs have been evaluated in tissue culture and exhibit an anti-cancer effect that is expected to have the same effect in a mammalian subject.

Therefore, FABPs, which are crucial intermediates in transmitting the signals of potent bioactive lipids, are logical targets a) for understanding the progression of tumorigenesis, b) as potential markers and c) for designing therapeutic regimens for prostate cancer.

DESCRIPTION OF FIGURES

Data from Breast Cancer Cells:

FIG. 3 shows a graph of Adipose-FABP findings: Adipose-FABP is same as the MDGI (mammary derived growth inhibitor) and the expression of this FABP is downregulated in cancer cells. The normal levels of Adipose-FABP is downregulated by 5–6 fold in cancer cells;

FIG. 4 shows a graph of CRAB-1 findings: The levels of cellular retinoic acid binding protein (CRABP) expression remains the same in cancer and normal cells. The levels of this FABP do not change with the stage of cancer;

Figure 5:
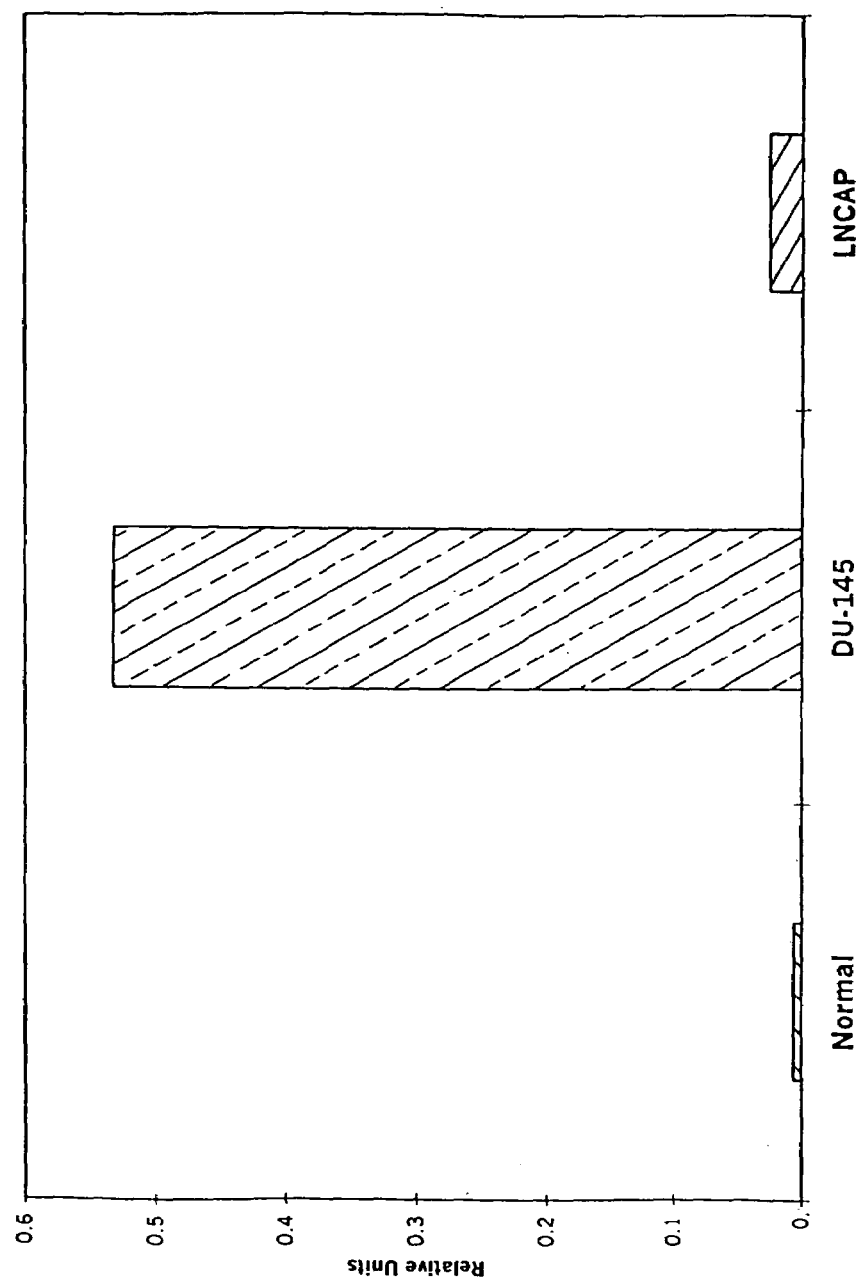
Figure 6:
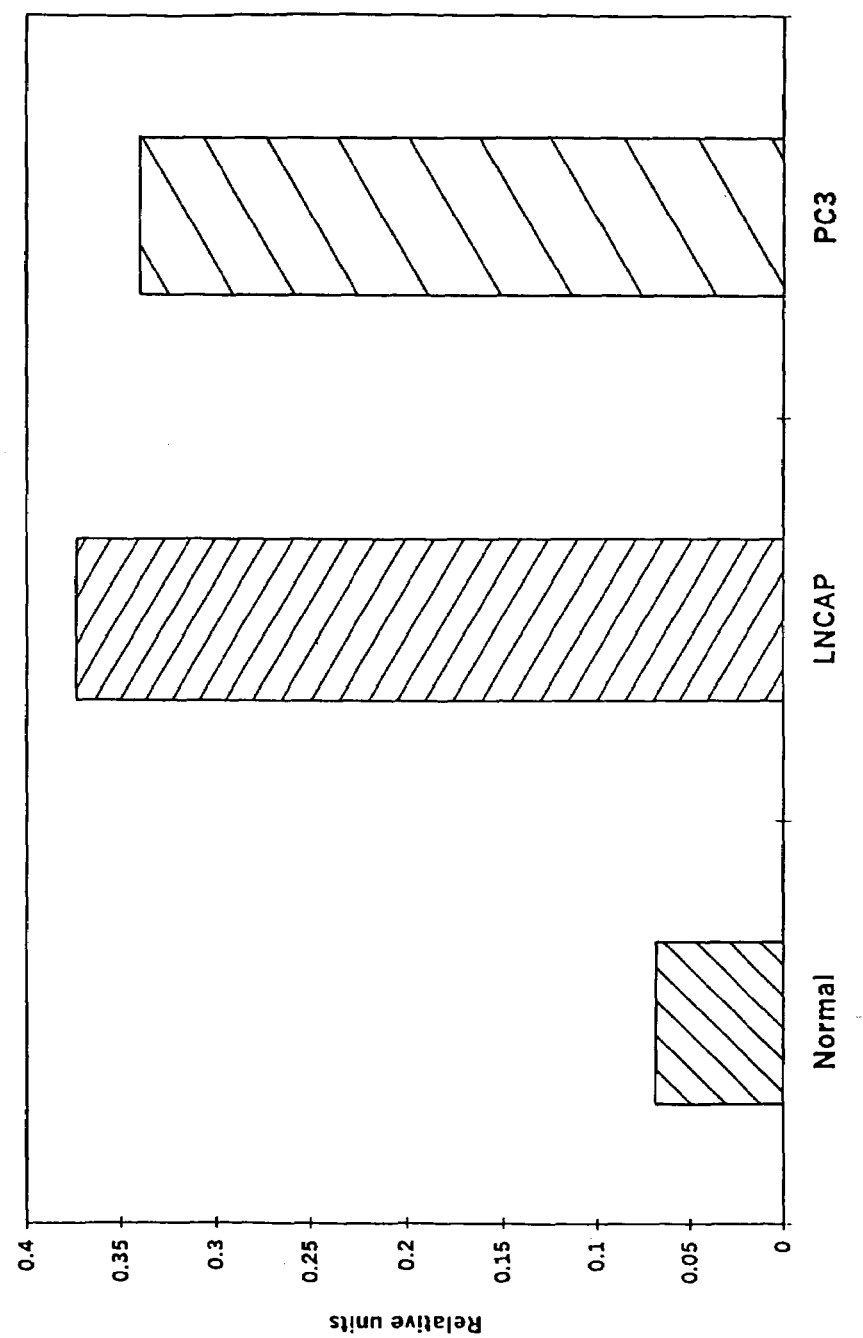
Figure 7:
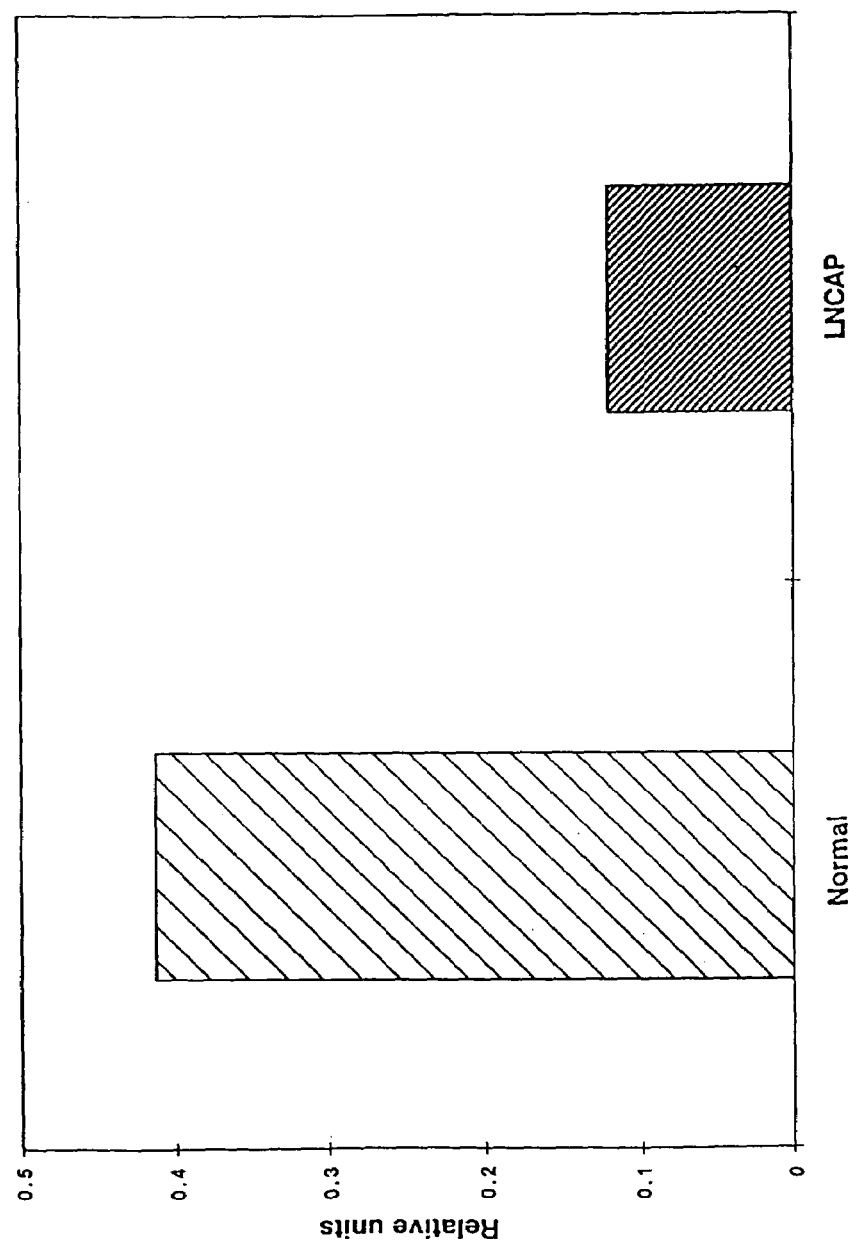
Figure 8:
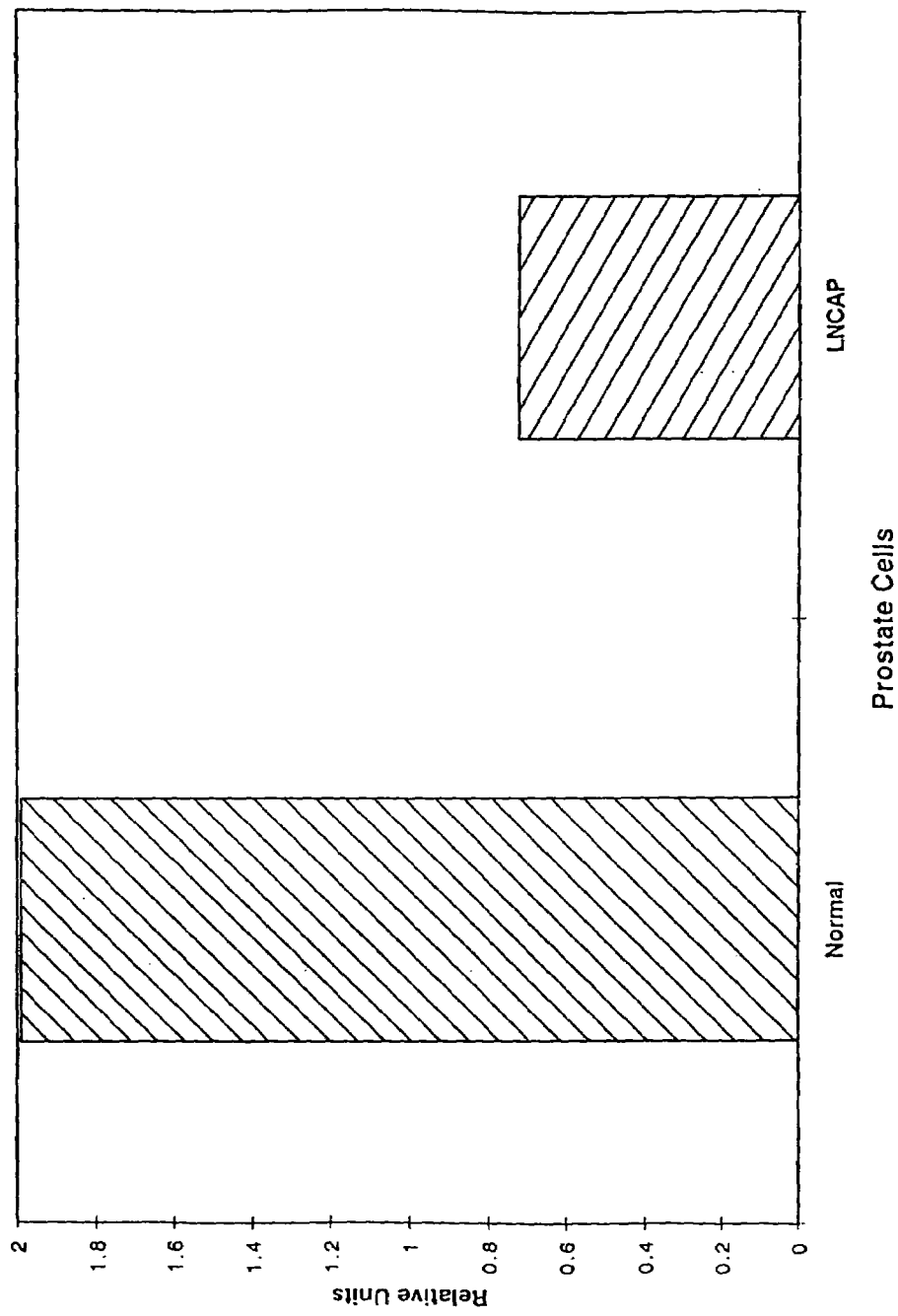
Figure 9A:
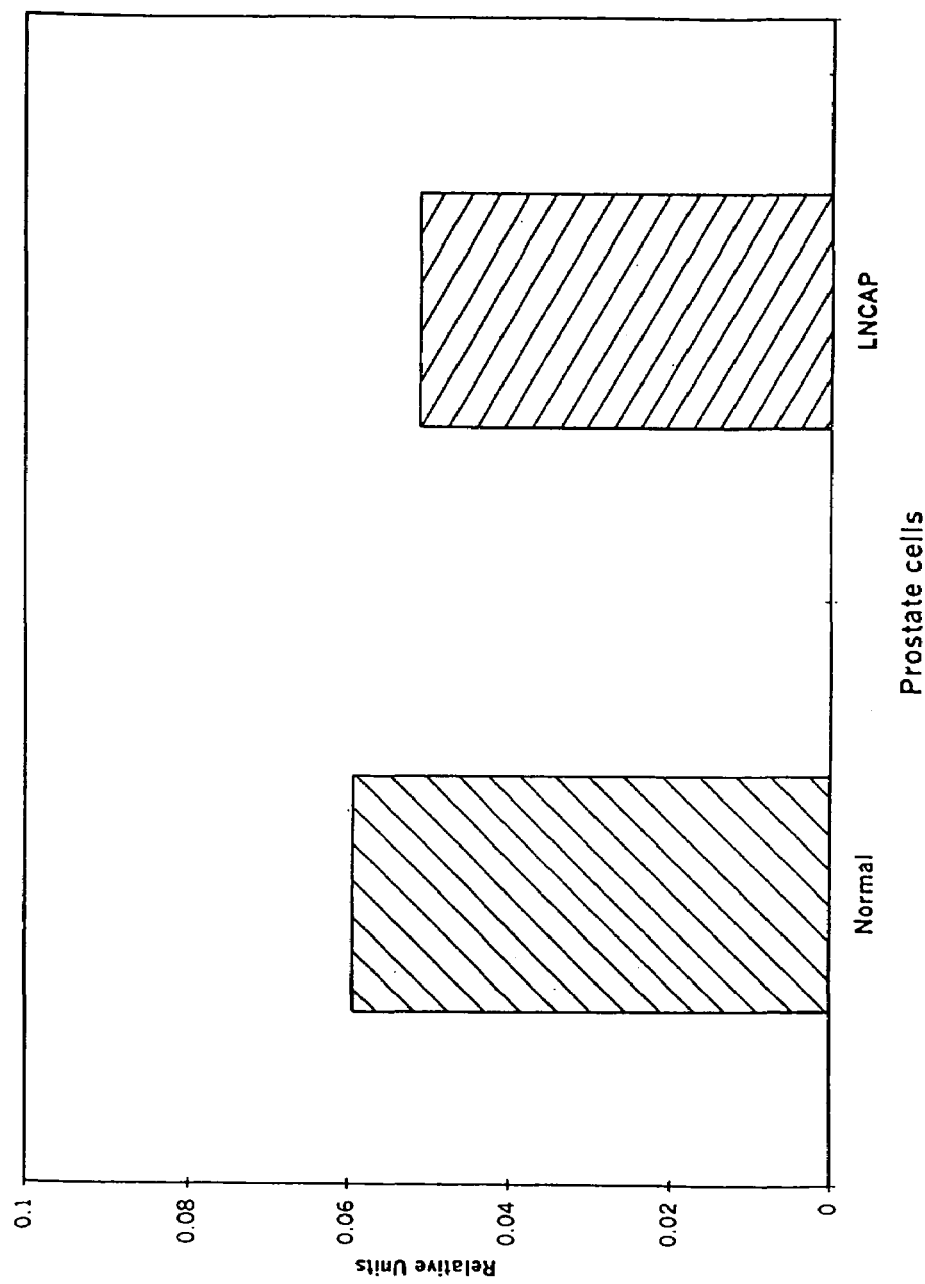
Figure 9B:
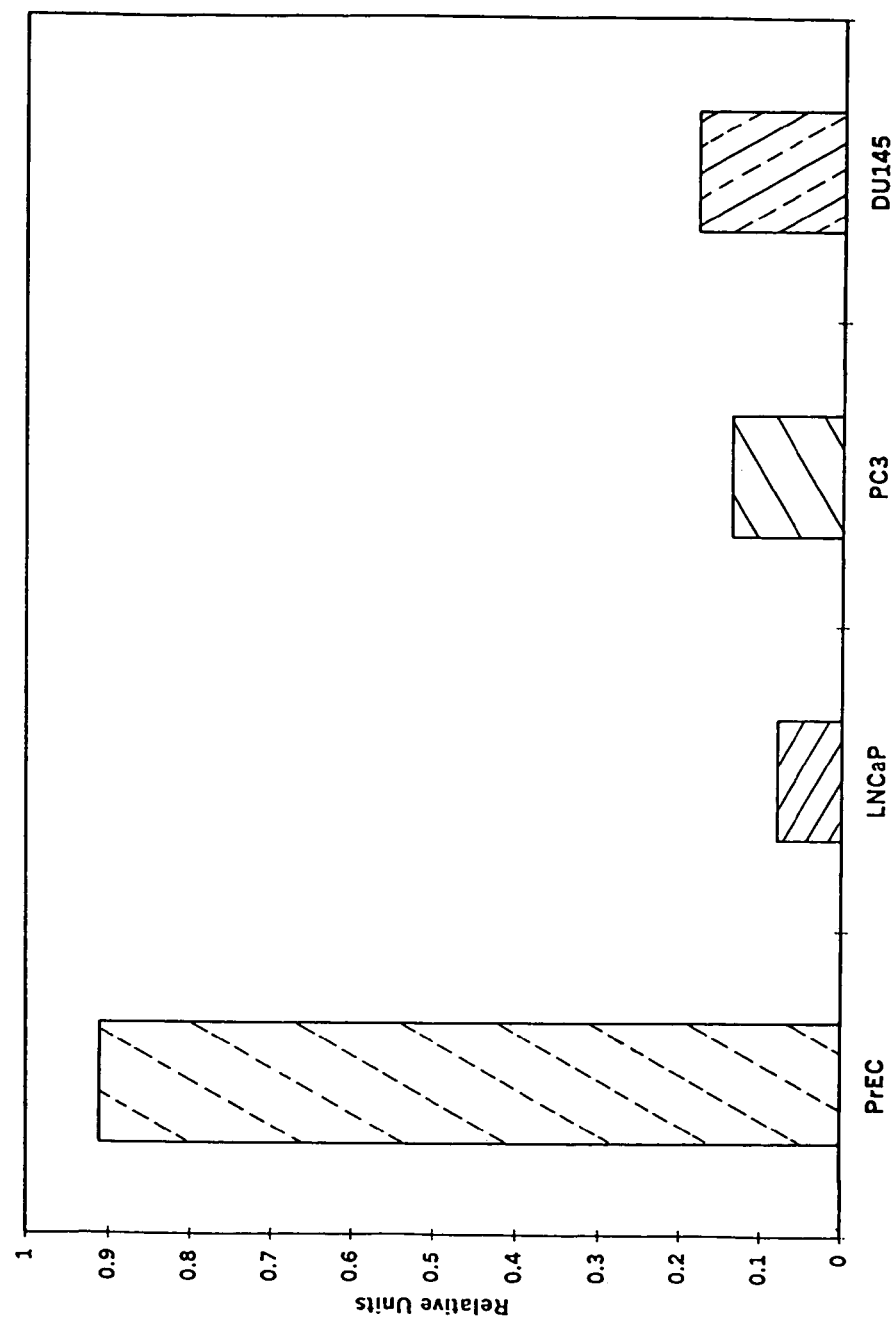

Data from Prostate Cells:

FIG. 5 shows a graph of Liver-FABP findings: In prostate cells only DU-145 cells expressed Liver-FABP, all other cells were negative for L-FABP. There was a 10 fold difference in normal versus DU-145 cells in expression of L-FABP;

FIG. 6 shows Intestine-FABP findings: The normal cells expressed very low levels of I-FABP, there was a 4–6 fold increase in expression of I-FABP in LNCAP cells which are prostate cancer cells;

FIG. 7 shows a graph of Muscle-FABP findings: The levels of Muscle-FABP was high in normal cells when compared to the cancer cells. The difference in levels was 4–6 fold;

FIG. 8 shows a graph of Adipose-FABP findings: The expression levels of Adipose-FABP was much higher in normal prostate cells when compared to the LNCAP cells. There was a five fold decrease in the expression of Adipose-FABP in cancer cells;

FIG. 9 shows a graph of CRAB-1 findings: The levels of CRAB-1 expression did not change in normal and cancer prostate cells;

FABP Levels in Human Tissue Samples from Patients:

Normal and cancer prostate tissue samples were staged by a pathologist at the VA-Pittsburgh hospital.

Figure 10A:
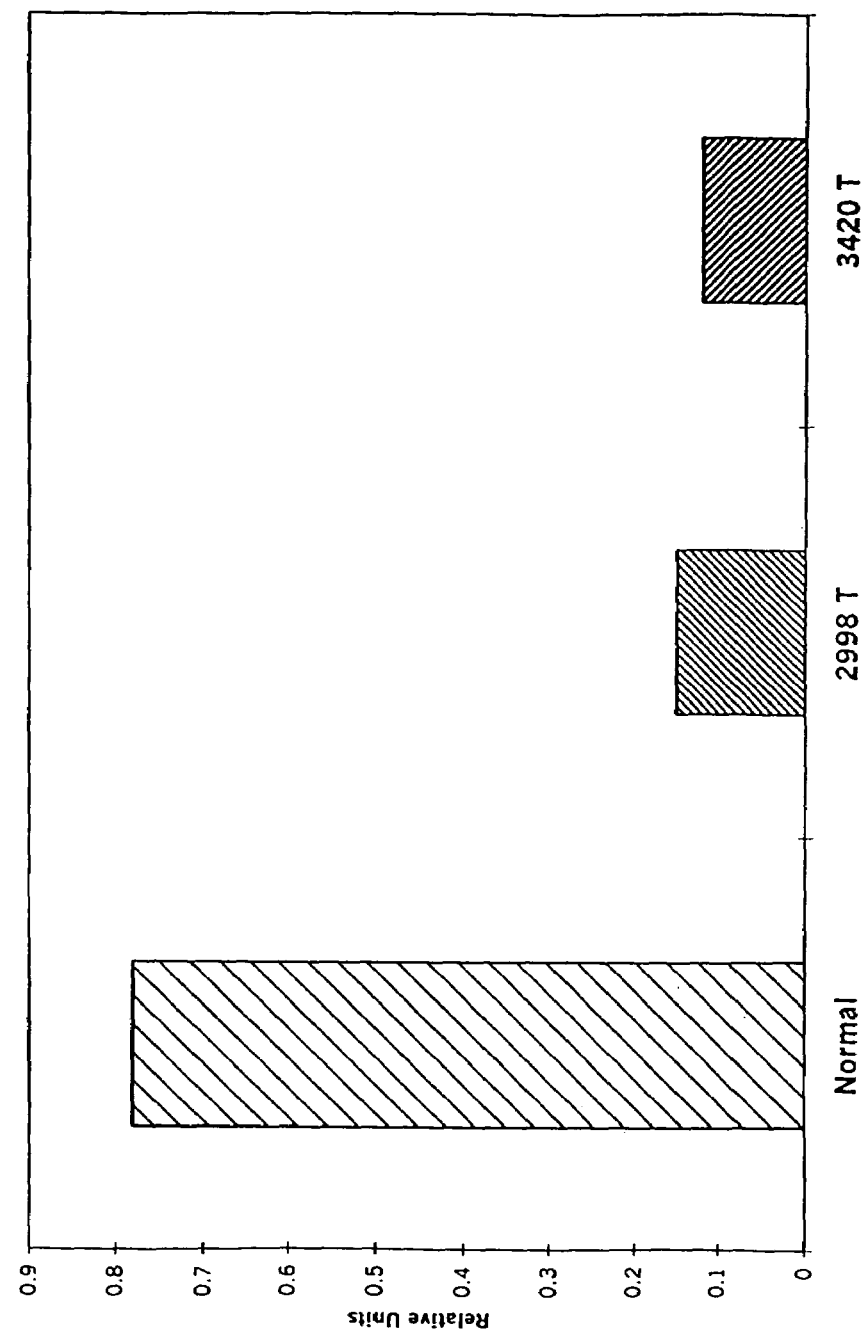

FIG. 10a shows a graph of Adipose FABP. This FABP was found to be highly expressed in normal tissue and its expression was >7 fold lower in prostate cancer tissue samples.

Figure 10B:
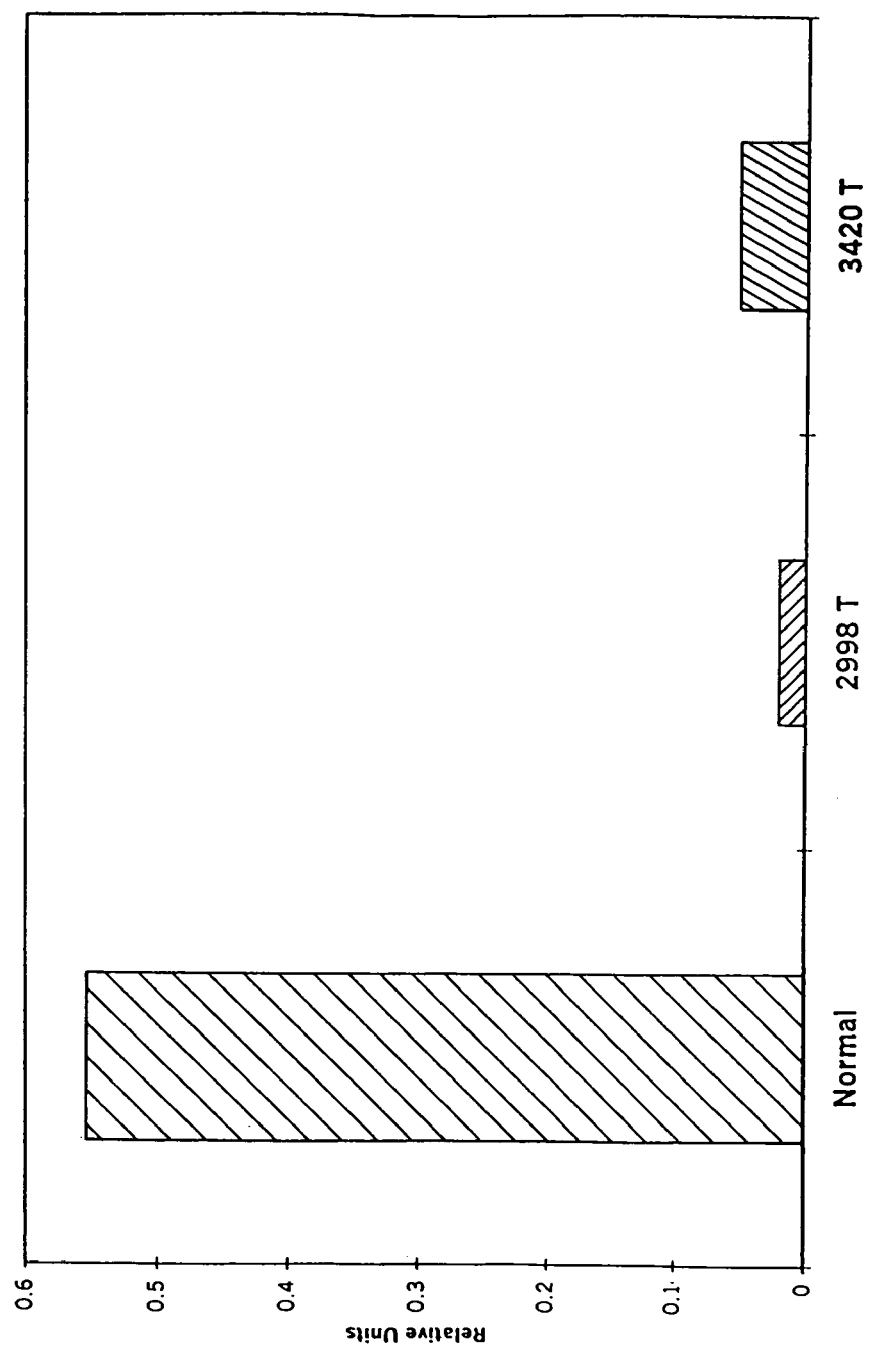
Figure 11:
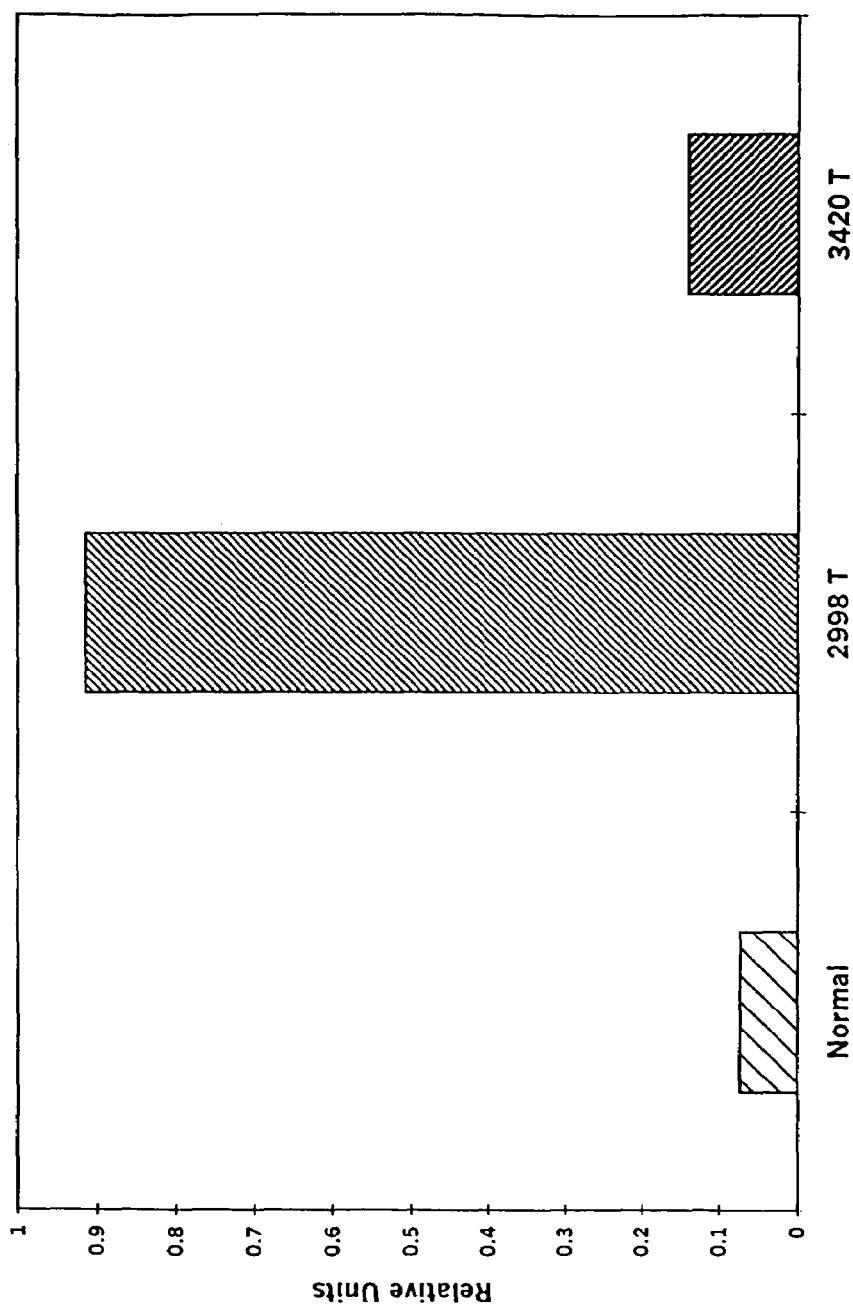

FIG. 10b shows a graph of Epidermal FABP: This FABP is found in parallel with adipose FABP. It is 3–5 fold lower in tumor samples than in normal prostate tissue. A similar observation was made for cultured prostate cell lines. The levels of expression of A-FABP and E-FABP was dramatically decreased in tumor samples when compared to the normal tissue sample;

FIG. 11 shows a graph of Brain FABP: This FABP was highly elevated in one of the prostate cancer samples, but not in the other one or in normal prostate tissue from patients. The expression of brain-FABP was very high in only one of the patient number 2998. Our studies with staged cell lines suggest that Brain FABP may be indicative of a more aggressive prostate cancer.

Data from Use of HPA Drug:

Structure of the Class of Drug

Figure 12A:
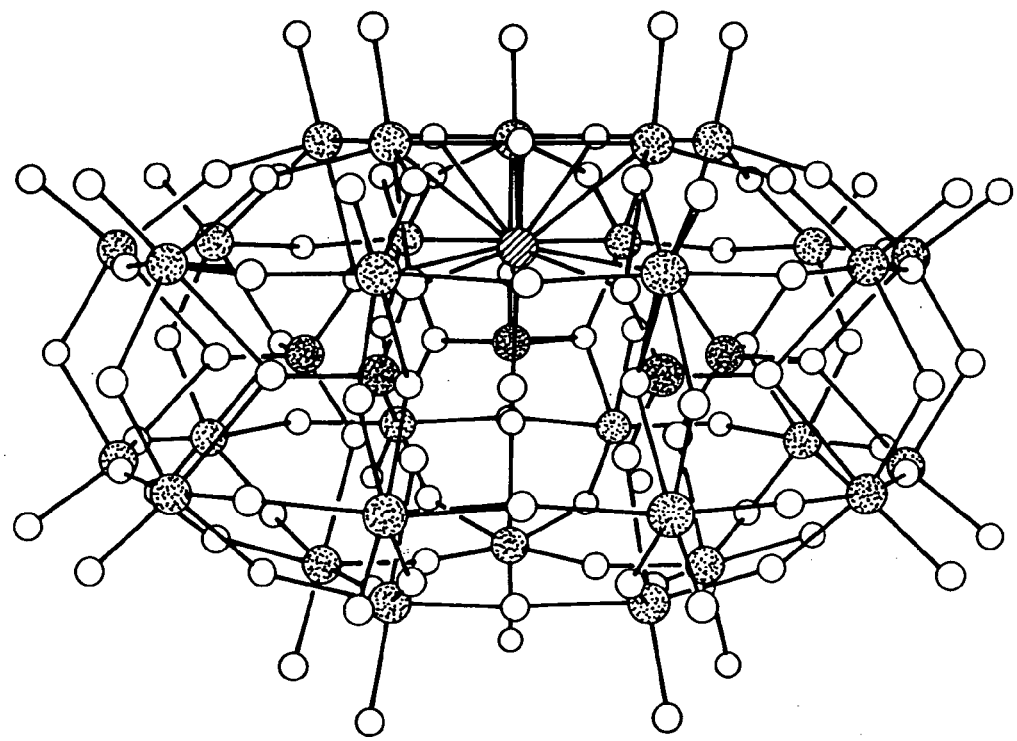
Figure 13A:
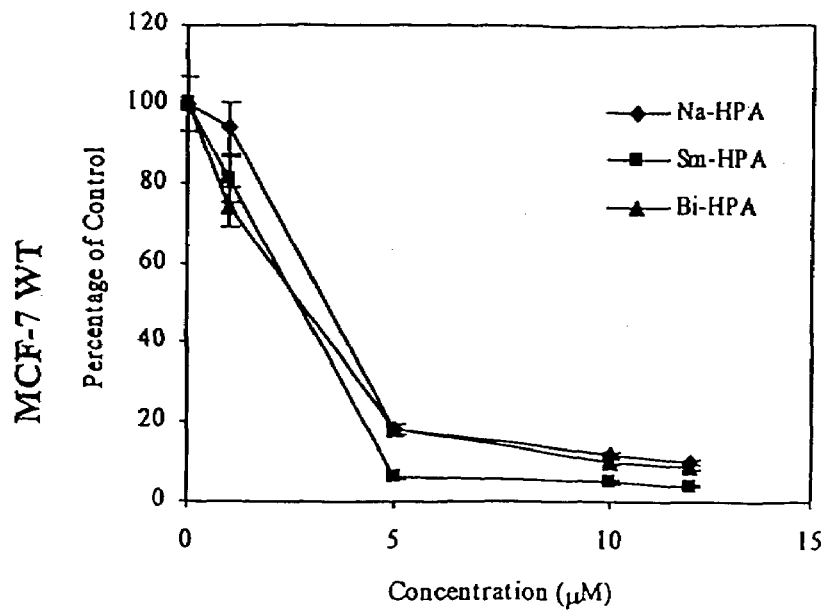
Figure 13B:
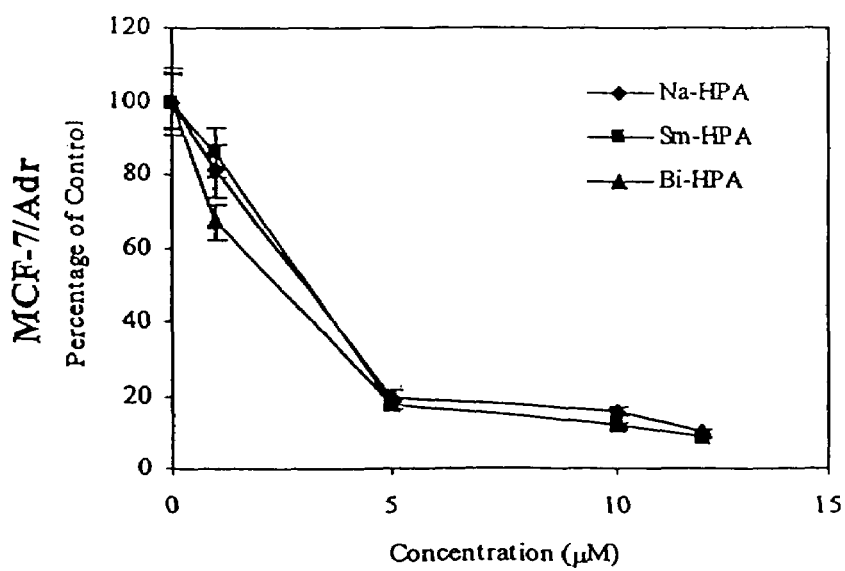
Figure 14:
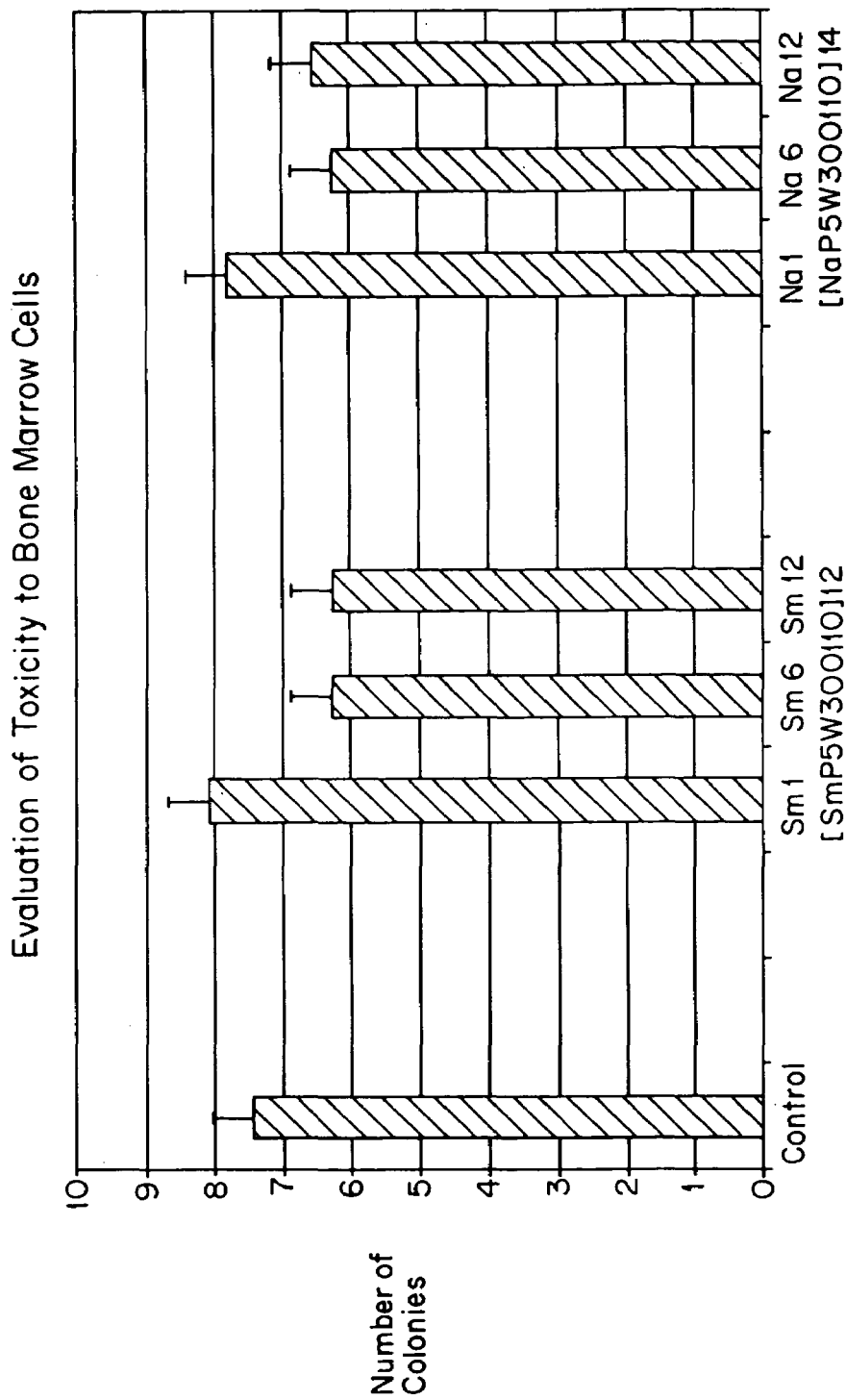
Figure 15:
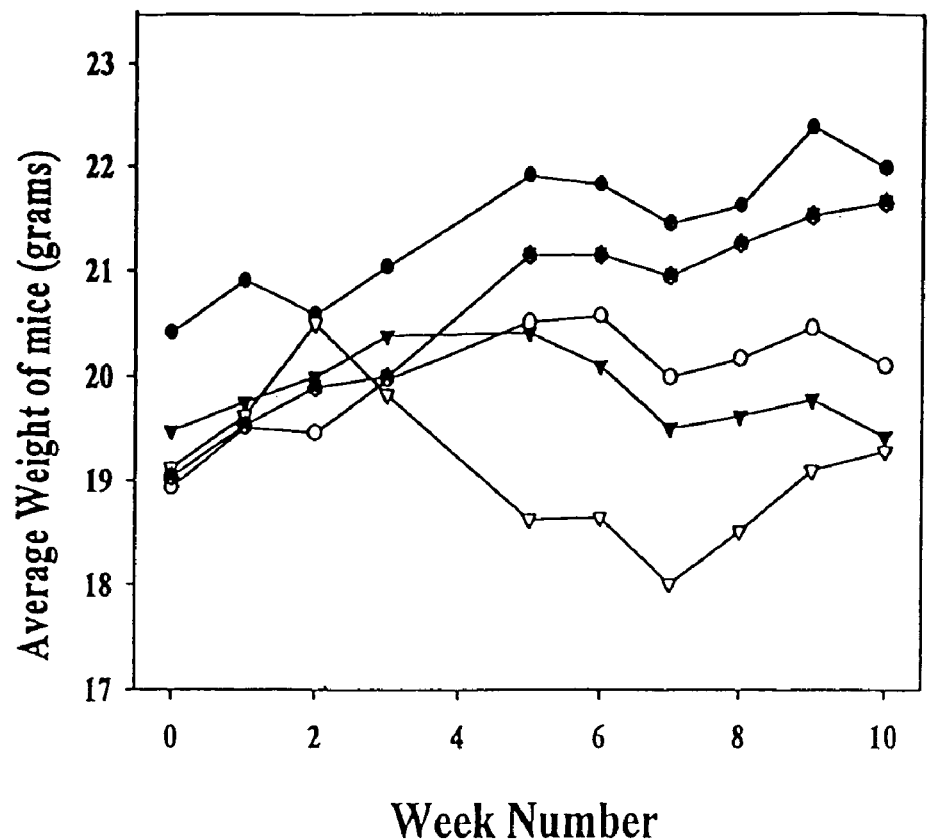
Figure 16:
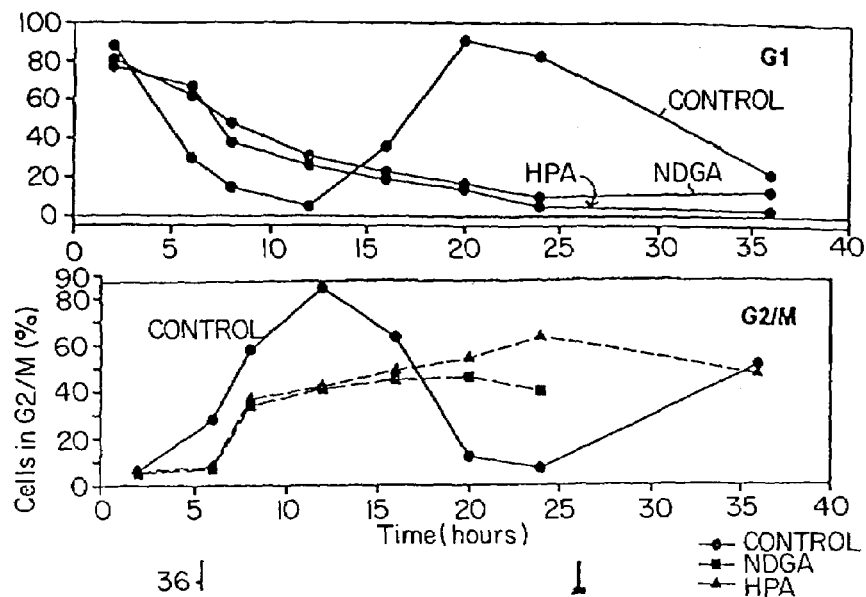
Figure 17A:
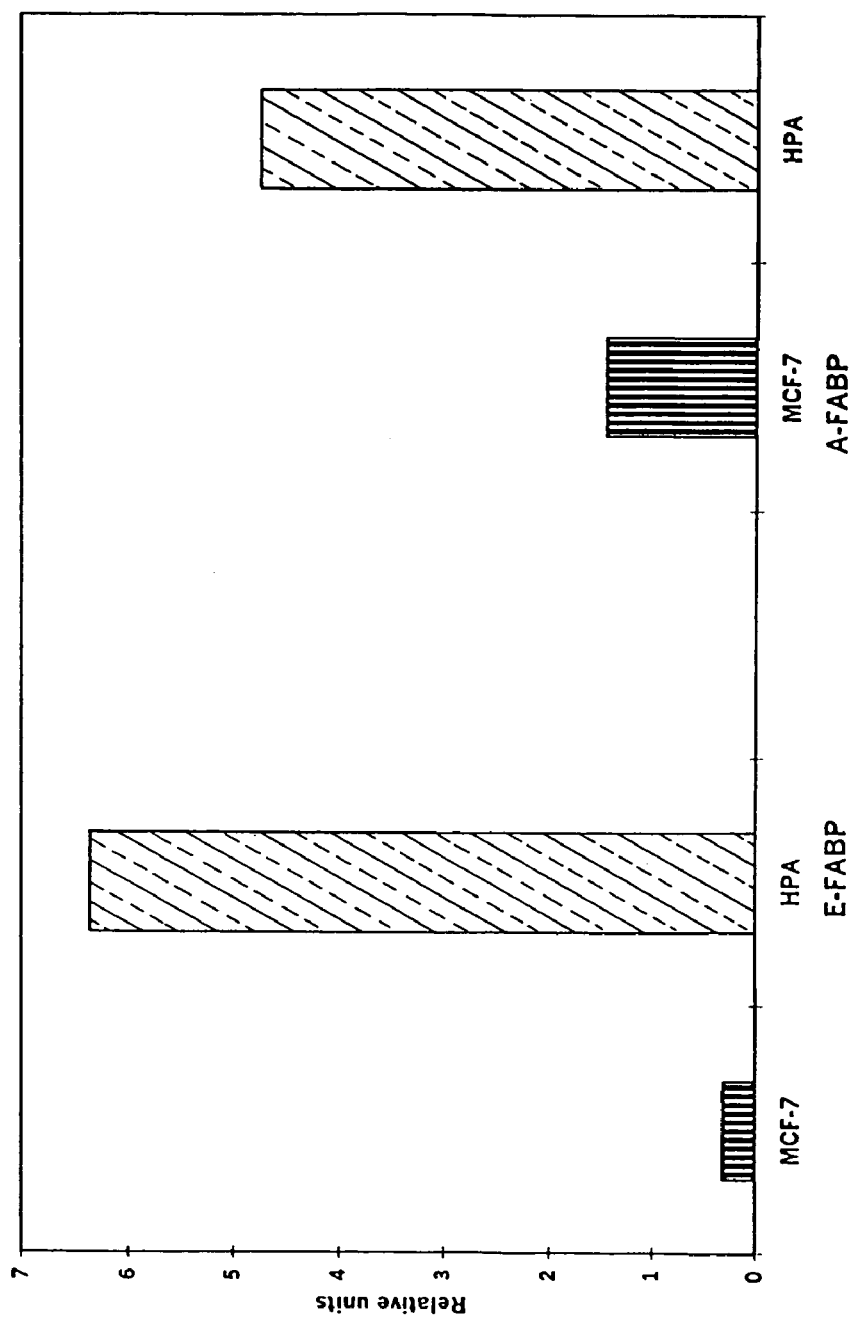
Figure 17B:
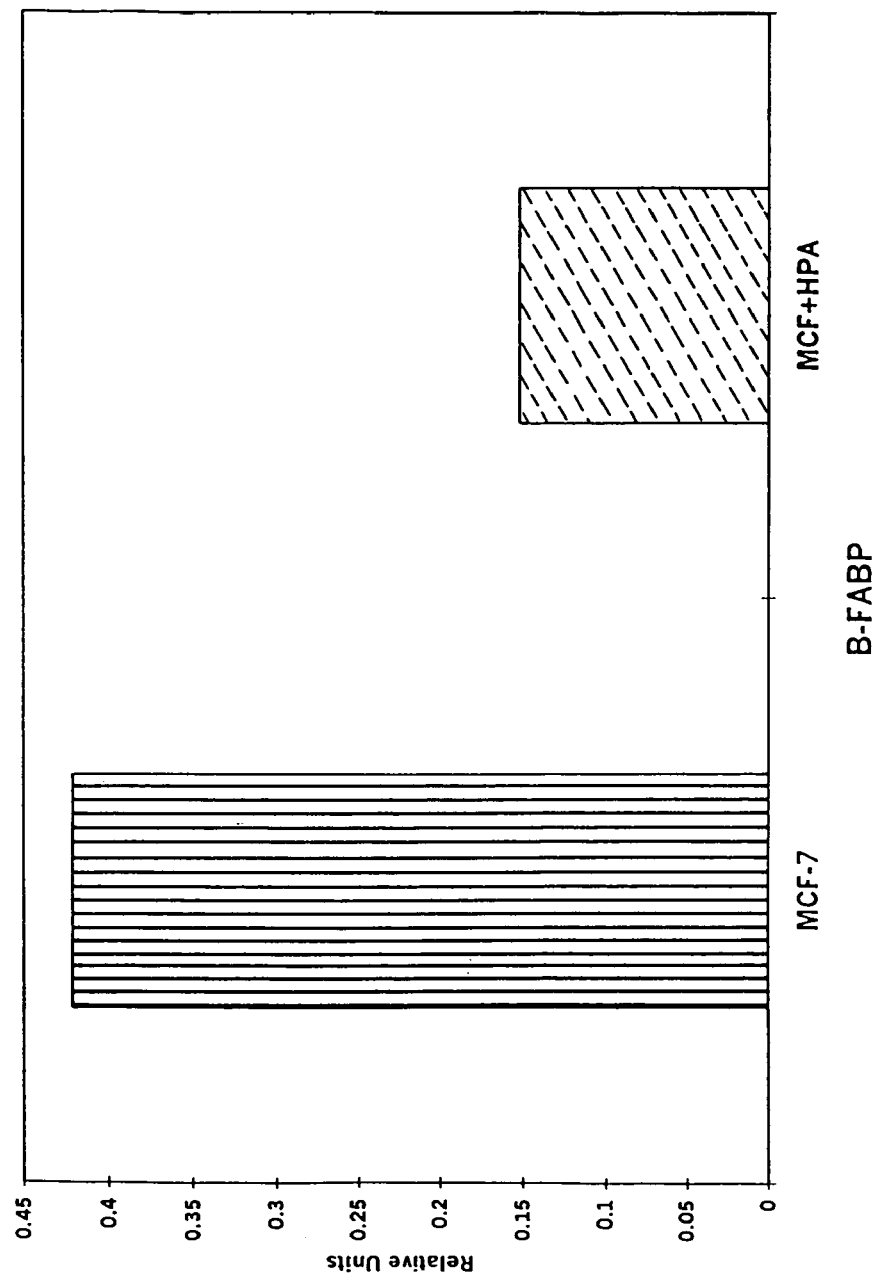
Figure 18:
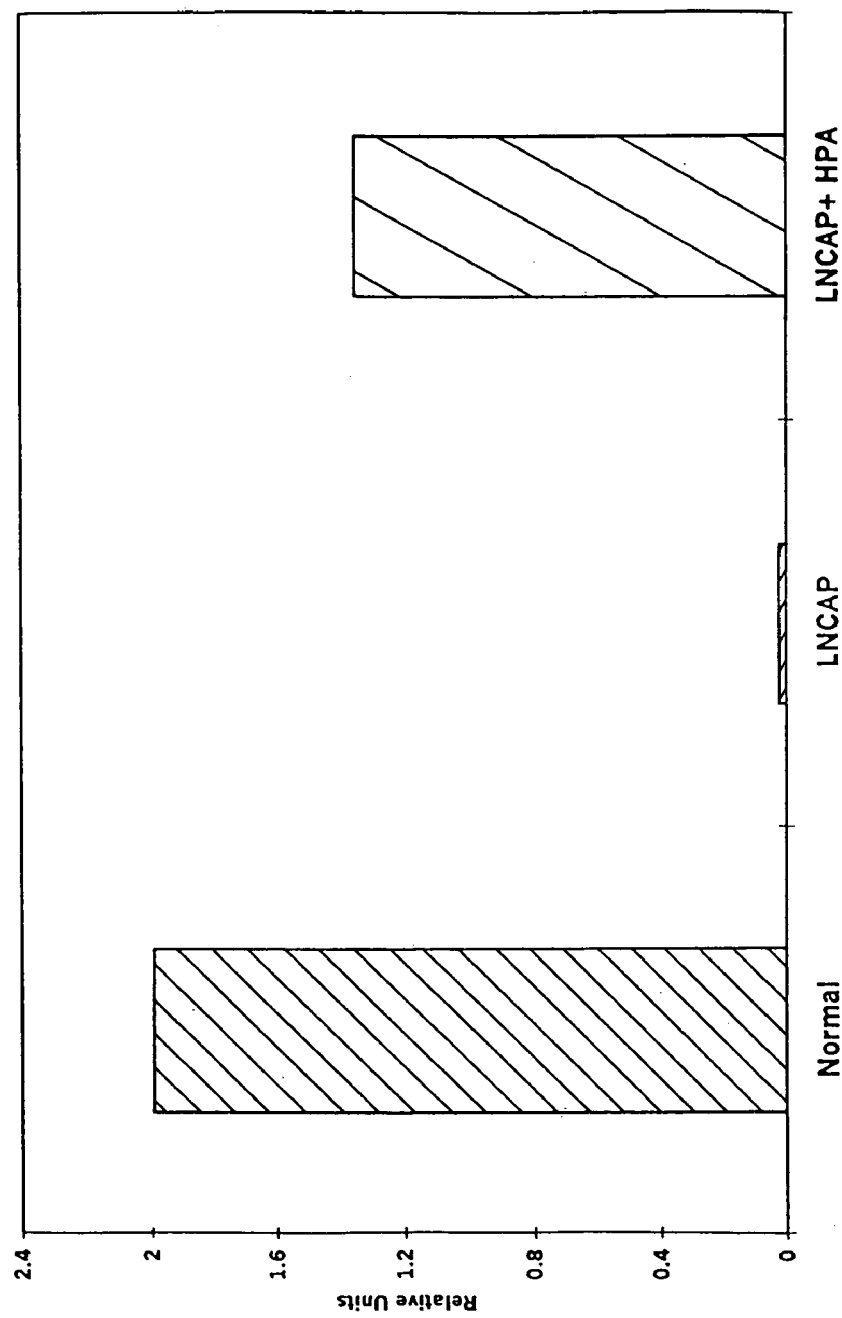
Figure 19:
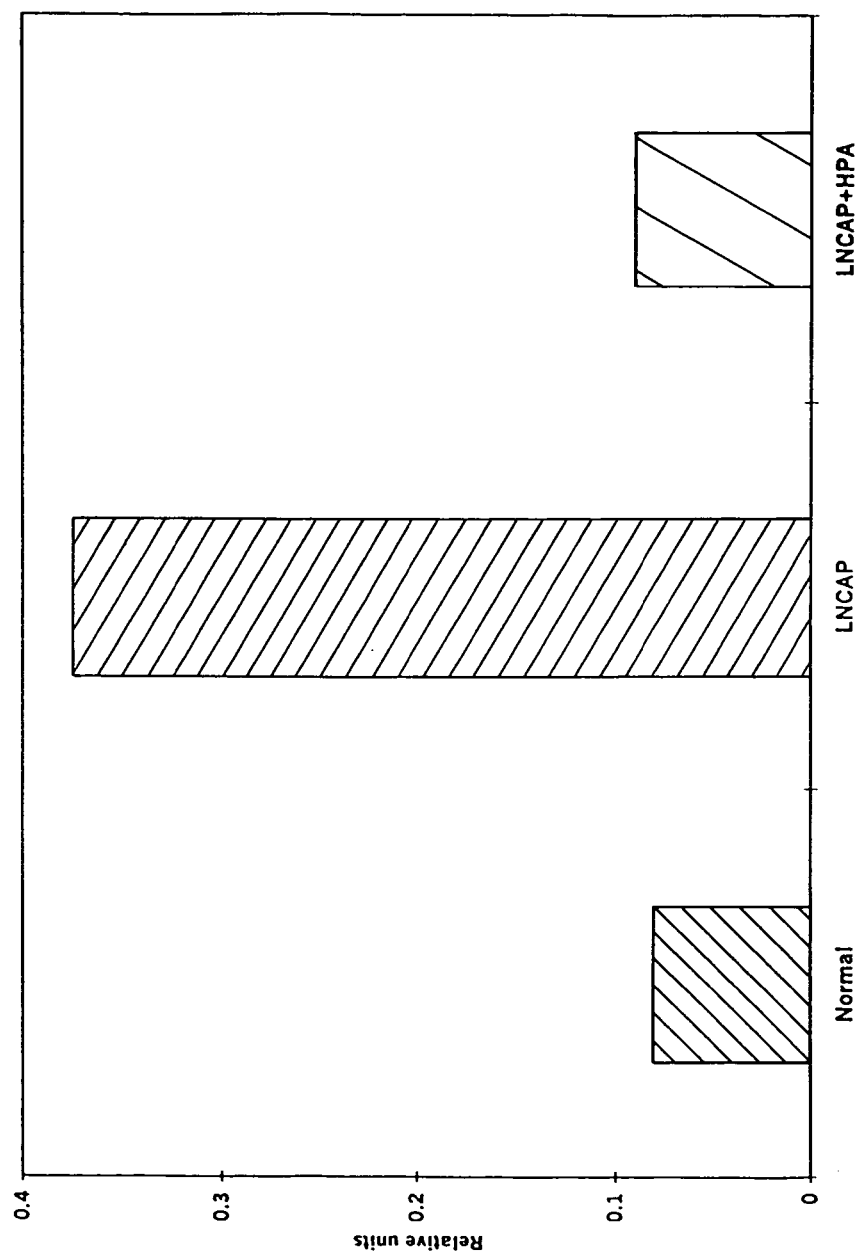

FIG. 12a shows the structure of the heteropolyanion drug (prior art) which is a polyoxotungstate free radical scavenger;

Concentration Curve of HPA on Growth of MCF-7 and MCF-7 ADR Cells:

FIG. 13 shows a graph of cells grown in the presence of different concentrations of these drugs and the cell number examined by cytofluor assay;

Effect of the Drug on Bone Marrow Toxicity:

FIG. 14 shows a graph of the human bone marrow stromal colonies grown in the presence of three concentrations of Na-HPA and the Sm-HPA for two weeks;

Toxicity Data in Mice:

FIG. 15 shows a graph of mice given indicated doses subcutaneously of HPA-Na weekly for 10 weeks and their weights were measured. Necropsies were performed and no indications of toxicity was observed;

Cell Cycle Data in the Presence of HPA and NDGA:

FIG. 16 shows a graph of cells synchronized by thymidine block for 12 hr. At that time the cells were washed and incubated in culture fluid alone or in the presence of the indicated drugs. For each of the drugs, cells became apoptotic by 28 h and the percentage increased through 36 h;

HPA and FABP Expression:

Changes in Expression of FABP in the Presence of HPA-Na in Breast Cancer Cells:

FIGS. 17a and 17b are graphs showing MCF-7 cells grown in the presence of 1 uM HPA-Na for 48 hr and RNA isolated for FABP measurement. E-FABP and A-FABP that was low in cancer cells dramatically increased when grown in the presence of the drug. However the levels of brain-FABP decreased significantly in the same cells in the presence of the drug;

Expression Pattern of FABP in the Presence of HPA-Na. Prostate Cancer Cells:

FIG. 18 is a graph showing LNCAP cells grown in the presence of 1 uM HPA-Na for 48 hr. At that time, cells were harvested, RNA prepared by the method of TRIZOL, and levels of various FABPs were measured by RT-PCR. In the presence of HPA-Na, the levels of A-FABP become markedly elevated and reflect the pattern observed in normal cell cultures. This suggests that HPA-Na has halted uncontrolled growth of the cancer cells and has caused them to advance to a stage of terminal differentiation;

FIG. 19 is a graph that shows the decrease in I-FABP in the presence of HPA-Na drug in LNCAP cells.

Figure 20:
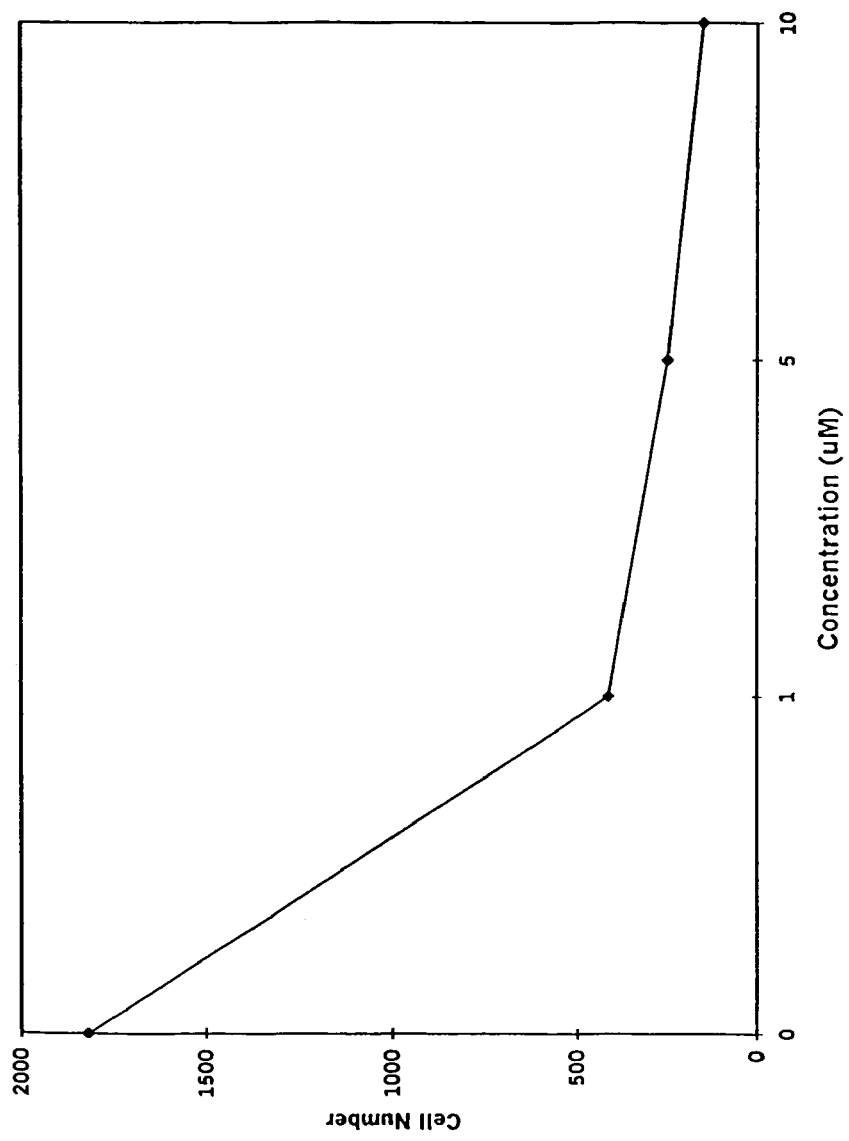

Effect of HPA-Na on Growth of LNCAP Prostate Cells:

FIG. 20 is a graph that shows cells grown in the presence of various concentrations of HPA drug for 48 hrs and the cell number determined using Cytofluor method.

DETAILED DESCRIPTION

Preferred Methods for Performing These Tests:

Measurements of RNA Levels of FABP in Breast and Prostate Cells/Tissue:

Established cancer cell lines were obtained from ATCC, Clonetics Corp., or were gifts from other scientists (Table 3). For each cell line, the culture fluid used was that described by the scientist who established the culture. Most of the culture fluids were obtained from Life Technologies, Gaithersburg, Md., or were obtained from the vendor from whom the cell cultures were purchased, if specialized additives were required. Primers were custom synthesized by methods known in the art with a reverse transcriptase kit obtained from Life Technologies. A standard PCR master mix was obtained from Boehringer Mannheim, Conn. PCR was performed by methods known in the art and as outlined in Methods in Molecular Biology, Volume 15, PCR protocols, current methods and applications, Edited by Bruce A. White, Humana Press, Totowa, N.J., incorporated herein by reference.

Cells from different stages of cancer were frozen (−70° C.) to keep the RNA intact. RNA was isolated using the well-established Trizol method. The amount of the RNA was estimated and frozen at −80° C. until further use.

For RT-PCR, equal amounts of RNA were used for the reverse transcriptase reaction to make cDNA. The cDNA was then used for the PCR reaction using specific primers for the different fatty acid binding proteins. Also, PCR was performed for genes such as Actin whose level stays generally the same in all the samples. The PCR products were resolved on agarose gel and the picture under UV was saved in the computer as a TIFF file. Using the NIH Image Program 1.6–1, gel optical units were digitized and obtained for each band observed. The values of the FABP PCR fragments were therefore normalized to the Actin values for each sample. In the figures, the data is represented in Optical Density Units versus the FABP and cell type from Breast and Prostate tissues.

For quantitative PCR, biotin labeled primers were used and a simple ELISA for quantitation of each sample was used by doing a concentration curve for each sample. These biotin labeled PCR products were quantitated using streptavidin coated antibodies (Streptavidin has very high affinity for Biotin) which was linked to HRP (Horse Radish Peroxidase) or a fluorescent tag that was used to measure the signals for each sample.

RNA levels can also be measured in body fluids by measuring stuffed off cells found in the fluids.

Measurement of Gene Changes by Using DNA Chips/Blots:

This is an innovative approach of analyzing changes in gene expression in a sample for a large number of genes simultaneously. The development of recent technologies permits the immobilization of DNA to a solid surface such as glass and exposure to a set of labeled probes; or an array of oligonucleotide probes are synthesized followed by on-chip mobilization. The array is then exposed to labeled sample RNA, hybridized and the positive signals analyzed. In this test, arrays of allele-specific oligodeoxynucleotides covalently attached to microscope glass slide through spacer linkers are used. Forty-eight oligonucleotides in duplicates can be attached to glass microscope slides in an area 2.5 cm by 0.75 cm with the use of a high speed arraying machine. Because allele-specific oligonucleotide probes for each mRNA are specifically chosen and synthesized in known locations on the arrays, the hybridization patterns and intensities can be interpreted in terms of the identity and the concentrations of various mRNAs simultaneously. Multiple oligonucleotides for each cDNA can be used to better quantify the concentration of mRNA.

Selection of allele-specific oligonucleotides for the array is critical for the specificity of the assay. Oligonucleotides specific to the FABP cDNAs can be selected using BLAST search programs. These will be spotted onto a solid surface and then they can be fixed, after which, one can hybridize RNA after labeling them with radioactivity or fluorescent dye and then wash the unbound RNA and then analyze the signals from these chips. A gene blot or a glass chip is developed that will have all the genes for the FABPs spotted on them. For diagnostic protocol, RNA is isolated from patient samples and label them and hybridize them to these blots. We will hybridize RNA samples from a normal patient and compare the differences of the cancer patient on the blots. This technique will allow us to measure the levels of all FABP at once.

Measurement of FABP Protein in Body Fluids:

FABP proteins are secreted into the serum. The levels of each type of these FABP proteins from the culture media of various cells were measured. From tissue culture, the conditioned media in which these cells are grown was frozen at −80° C. The media was processed several times to concentrate the media using molecular cut off filters. A 500K (Millipore, Mass.) cut off filters was used to eliminate proteins above that molecular weight, and a 3K cut off filter was used to eliminate proteins below that molecular weight. In this filtering process, the media was concentrated to one-tenth the initial volume. The amount of protein present was quantitated in the concentrate (Bradford method, Bio Rad, Calif.) and then ELISA was performed to evaluate the levels of the various FABPs by using specific antibodies to each of the different types of FABPs. Antibodies such as heart FABP antibody and Liver-FABP antibody obtained from Research Diagnostics, Inc., Pleasant Hill Road, Flanders, N.J. 07836 were used in these tests. However, antibodies for the remaining FABPS can also be developed and used. The levels of these proteins were correlated to the stages of cancer in tissue culture cells. Two antisera are available and specific for the protein.

By isolating serum from Breast and Prostate cancer patients, the inventors have evaluated the levels of these proteins in the serum and have correlated the amount to the stage of cancer. The test results for all the above along with CRAB-1, which does not change in normal vs cancer cells, are discussed below and are illustrated in the Figures.

It is also possible to measure FABP protein in tissue samples.

Detailed Description of Results: Breast Cancer.

There is a positive correlation between high dietary fat and development of breast cancer. In nude mice, diets high in corn oil, a fat rich in the AA precursor linoleic acid, markedly stimulated the growth of human breast cancer xenografts. Thus, it appears that arachidonic acid acts as a potent mitogen for human breast cancer cells. Fatty acid binding proteins (FABP) bind fatty acids noncovalently with high affinity and translocates them across the cell to the nuclear receptors. The existence of various FABP types and the relative abundance of these cytoplasmic proteins in nearly all tissues indicate important functions for these molecules.

Figure 1:
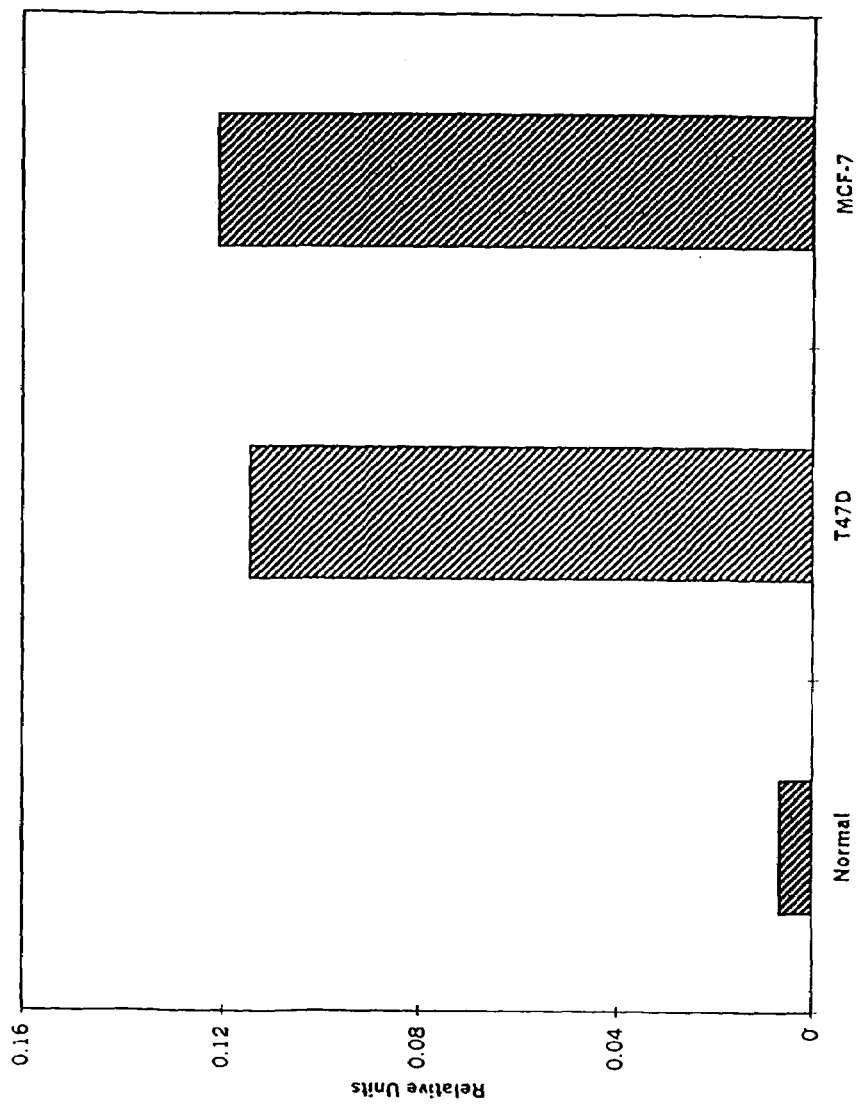
FIG. 1 shows a graph of Liver-FABP findings: L-FABP expression was very low in normal breast cells, it is almost absent in normal cells. The increase in L-FABP levels in breast cancer cells (T-47D & MCF-7) have been 12–15 fold higher compared to the normal cell values. Also we observed that the estrogen receptor positive cells had this change in levels of L-FABP, but no change was observed in few estrogen receptor negative cells that we have tested.

The inventors found that the level of L-FABP was 12–15 fold higher in cancer cells when compared to the normal breast cells. The increase of L-FABP is also implicated with liver carcinogenesis. The significant increase in the level of L-FABP gene in breast cancer cells that are estrogen receptor negative has never been shown before. The level of L-FABP in normal breast cells was undetectable or very low as shown in FIG. 1.

Figure 2:
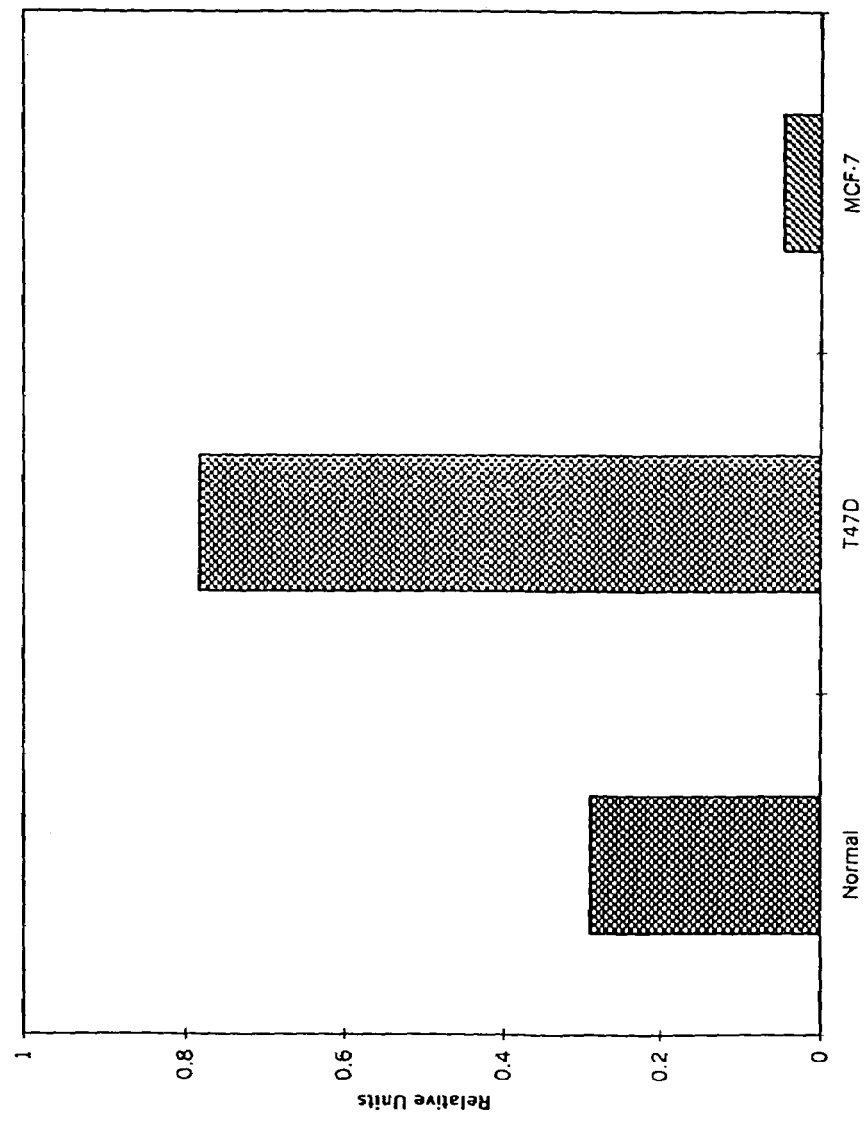
FIG. 2 shows a graph of Intestine-FABP findings: The expression of Intestine-FABP was also shown to be upregulated in breast cancer cells compared to the normal breast cells. There was a 4–6 fold increase in the level of I-FABP when compared to the normal cells.

The I-FABP and the L-FABP are very similar in their genetic sequences and their mode of action. They are both associated with tumor state. In breast cells the normal had low levels of this gene expressed, however only T47D showed significant high levels of expression of the I-FABP as shown in FIG. 2.

It was observed that Adipose-FABP, abbreviated A-FABP, acts like a tumor suppressor. With the progression of the tumor, a gradual loss of the expression of this gene was observed. In normal breast cells a high level of expression of A-FABP was observed and A-FABP were very low in T47D and MCF-7 cells. Loss of A-FABP was reported with progression of human bladder transitional cell carcinoma. The presence of A-FABP thus correlated with the grade and stage of the disease. Our results also support that A-FABP is expressed in high levels in normal cells and it is significantly downregulated in tumor cells.

Cellular retinoic acid binding protein is another class of FABP that is known to be regulated by fatty acids. The levels of the gene were measured and no significant difference in normal breast and breast cancer cells was observed, as shown in FIG. 4. This suggests that not all FABPs are altered in normal and tumor state. Some proteins remain unchanged, at least at their message levels.

The inventors have analyzed the role of FABPs in breast cancer. Nothing was known about the levels of FABPs in different stages of breast cancer, or the effect of hormones, growth factors or bioactive lipids on FABPs. The inventors have shown that FABP message (Liver and Intestine type) is 3–22 fold higher in tumor vs normal breast cells, especially in the estrogen receptor positive lines. The inventors have also shown that the A-FABP, E-FABP class of proteins are downregulated in breast cancer cells.

Since FABPs are also secreted into the surrounding fluid, they can be identified in human fluids such as semen, saliva, blood and urine samples.

Detailed Description of Results: Prostate Cancer.

The transition of prostate cancer from slow growing, localized disease to a rapidly growing metastatic tumor appears to be influenced by circulating hormones and dietary fat. PCR analysis using primers for 5 types of FABPs, especially adipose, intestine and liver, were employed to quantitate levels of FABP expressed in prostate normal and cancer cell lines. The expression pattern of A-FABP in prostate normal and cancer cells was studied. Normal PrEC cell line from Clonetics was grown in culture and RNA obtained, LNCAP, PC3 and DU145 were also grown in culture to obtain total RNA from them. RT-PCR was performed using A-FABP specific primers, the product was resolved on the gel and analyzed by NIH Image program for quantitation. The values were normalized to the actin values. A dramatic (10–14 fold) decrease in the A-FABP message in cancer cells was observed when compared to the normal prostate cells as shown in FIG. 8. In some of the cancer cells the expression of A-FABP was undetectable which corresponds to an advanced stage of cancer. Similar results were observed with breast cancer cells.

The expression of E-FABP in prostate normal and cancer cells was studied. When RT-PCR was performed for the E-FABP gene, the expression pattern was similar to the A-FABP. It decreased 10–14 fold in cancer cells when compared with the normal prostate cells as shown in FIG. 10. The PCR product was also sequenced with a cycle sequencing kit (Amersham Corp, Piscataway, N.J.) and it matched with human E-FABP sequence. Thus with the progression of the cancer, the levels of E-FABP went down significantly in prostate cells. The level of expression of E-FABP was the most predominant when compared with all the other FABP levels in the prostate cells.

The expression of L-FABP in prostate cells was studied. L-FABP gene expression was elevated significantly in the cancer cell DU 145 when compared to the rest of the prostate cells as shown in FIG. 5. DU 145 is a metastatic prostate cell line and thus high levels of L-FABP may corresponds to the aggressiveness of the prostate cancer.

The expression of I-FABP in prostate cells was studied. The expression of the intestine type of FABP was tested in prostate cells. As shown in FIG. 6, a dramatic increase in expression of the I-FABP in cancer cells was observed when compared to the normal prostate cells. Since I- and L-FABP are similar in their sequences and also are found to be elevated in cancer cells, these proteins act as biomarkers for prostate cancer.

The expression of Mus-FABP in prostate cells was studied. When RT-PCR was performed with Heart/Muscle type of FABP that is in the same family of proteins as the Adipose-FABP, a similar trend in the levels of this FABP was observed. It was high in the normal prostate epithelial cells and was dramatically low in LNCAP, prostate cancer cells as shown in FIG. 7. This suggests that the heart type of FABP also has a tumor suppressive role in prostate cancer cells.

A similar protein in breast has been studied in great detail called the MDGI (mammary derived growth inhibitor). MDGI and the heart type of FABP are identical in their sequence and behave the same way. MDGI has been shown to be present in normal lactating breast and disappears with progressive stage of cancer.

The Expression of Brain-FABP in prostate cells was studied. The expression of all the different types of FABP in these prostate cells was further tested by performing RT-PCR for brain-FABP. Only the LNCAP cancer cell line was positive for B-FABP. All other cell lines were negative for the expression of the gene.

Because they bind bioactive lipids which initiate signals that result in increased mitogenesis, FABPs are believed to play a crucial role in promotion of prostate cancer cell growth. The members of this broad multigene family currently consist of at least seven types whose amino acid sequences have been obtained from protein purified from tissue or from cDNA nucleotide sequences from tissue RNA. The designations for each of the FABPs is derived from the human tissue from which it was isolated and includes: 1) adipocyte (A-FABP), 2) heart or muscle (H-FABP), 3) brain (B-FABP), 4) epidermis or psoriasis-associated (E-FABP), 5) liver (L-FABP), 6) intestine (I-FABP), and 7) myelin or P2 (P2-FABP). As a group A-FABP, H-FABP, B-FABP, and E-FABP in humans share between 50–65% protein sequence homology and contain a tyrosine near residue 20 that can be phosphorylated. These four FABP share only 20–25% homology with L-FABP or I-FABP which do not have the tyrosine. Heart-FABP and Muscle-FABP differ only in three amino acids and therefore can be referred to as Muscle/Heart-FABP. A test for Heart-FABP will also test for Muscle-FABP.

The inventors have examined the levels of FABPs in several normal prostate and cancer cell lines in order to establish a correlation between presence and levels of FABP with the stage of cancer represented by each cell line. The levels of 5 selected FABPs were analyzed using primers designed for RT-PCR and have found their expression to be altered in prostate cancer vs normal cells.

Changes of FABP in human tissue samples was studied. Tissue samples were obtained from the VA-Pittsburgh Hospital. These samples were graded by a pathologist for the stage of cancer before they were frozen and sent to the inventors. The inventors then isolated the RNA and examined by RT-PCR the levels of several of these FABPs. There was significant change in the levels of A-FABP and E-FABP. Both these FABPs were very high in the normal sample and was very low (3–8 fold) in tumor samples. The level of Brain-FABP was also upregulated 10–14 fold in one of the patient sample. This suggests that the changes in FABPs identified in cultured prostate cells are consistent and has been confirmed from patient samples of prostate cancer. We also propose to test these FABP levels in a large number of human tissue samples to confirm our findings.

Use of HPA Drug for Breast and Prostate Cancer Cells:

We have identified a class of heteropolyanions that have anticancer activity. This class consists of metal ion derivatives of polyoxotungstate, hereinafter referred to as HPA. These heteropolyanions (HPA) are synthesized by methods outlined in Heteropoly and Isopoly Oxometalates, Michael Thor Pope, Springer Verlag, Berlin, Germany 1983. They are water soluble and stable at room temperature and are effective at very low concentrations (1 $\mu$M) in cell cultures. Mice have been given HPA drug subcutaneously at doses up to 28 mg/kg for 3 consecutive weeks or 12 mg/kg for 12 consecutive weeks. Oral and intramuscular administration were also tested. Drugs were dissolved in aqueous solutions for administration. Preferred HPA drugs are HPA-Na and HPA-Sm.

A whole panel of this class of drugs have been tested in breast cancer cells, MCF-7. We have shown that this drug was able to block the growth of breast cancer cells that are wild type and also the drug resistant MCF-7 ADR cells. This allows the use of this drug when the patient starts showing drug resistance to the commonly used chemotherapeutic drugs. This drug is nontoxic to mice when tested for any change in body weight or by necropsy studies. This drug is also not toxic to human bone marrow cells, which are effected the most during chemotherapy.

We have shown that these HPA drugs not only block the growth of cancerous cells but also alter the levels of FABPs to resemble the levels FABPs in normal cells. Use of HPA-Na (1 uM) increased the levels of A-FABP in LNCAP to a level similar to the normal values as shown in FIG. 10. The levels of E-FABP was also altered in a similar manner. The level of I-FABP of LNCAP cells was dramatically reduced to the normal level in the presence of this class of drug as shown in FIG. 11. Similar changes in pattern of these FABPs were also observed in breast cancer cells MCF-7, when they were grown for 48 hrs in the presence of this drug.

We have shown that the HPA drug is able to block the cell cycle of MCF-7 cells in a particular phase (of cell cycle) which ultimately results in terminal differentiation and apoptosis.

The heteropolyanion drugs can be used alone or in combination with inhibitors of eicosanoid metabolism on the growth of breast cancer cells. Inhibitors contemplated are those currently used in clinical situations such as doxorubicin, 5FU, vinca alkaloids, adriamycin as well as lipoxygenase inhibitors. The HPA drug can be given simultaneously with or can be given followed by exposing the cancerous cells to one or more applications of an amount of HPA containing metal ions, preferrably HPA-Na, in an amount sufficient to block the growth of the cancerous cells and change the FABP profile to a normal cell FABP profile. Subsequent applications of chemotherapeutic agents or inhibitor can be given in a lower amount than previous applications.

Thus, these HPA drugs have efficacy for use as an anticancer agent. It has a great potential, not only for stopping growth of cancer cells but also for changing the balance of the FABPs that play a role in carcinogenesis.

The detection protocol used to identify prostate cancer-elevated FABPs in human blood, urine or semen samples from patients showing elevated prostate specific antigen (PSA) levels is as follows.

EXAMPLE 1

PCR and DNA Sequence Analysis of FABP Expression in Prostate Cells.

(a) PCR analysis using primers for 5 types of FABPs, especially adipose, intestine and liver, were employed to quantitate levels of FABP expressed in prostate normal and prostate cancer cell lines. A panel of prostate normal and cancer prostate lines obtained from the cell/tissue bank (ATCC, Clonetics) were tested for the presence of FABPs. The normal immortalized prostate cell line PZ-HPV-7, was grown in Keratinocyte-serum free media, all other cells were grown in serum containing media. Several primary cultures of normal prostate cells were obtained from Clonetics Corp. Prostate cancer cell lines such as LNCaP, PC3, DU145 were obtained from ATCC.

RT-PCR for FABP Genes:

The RNA was isolated using the Trizol method and RT-PCR analysis of the proteins was performed by using primers specific for each FABP. Equal amount of RNA was used for RT-PCR and PCR master mix was used to avoid any handling errors. The sequence for FABPs was obtained from the gene bank and the GCG program (GCG program is well know) was used to design specific primers. The method of quantitation of PCR product was as follows: for internal quantitation control actin primers was used, all the gels were scanned in a gel scanner and digitized using the NIH-Image program for quantitation. Each band for the respective FABP was then normalized with the actin value and then comparison made between prostate normal and cancer cells.

Data from Breast Cancer Cells:

Liver-FABP: L-FABP expression was very low in normal breast cells, it is almost absent in normal cells. The increase in L-FABP levels in breast cancer cells (T-47D & MCF-7) was 12–15 fold higher compared to the normal cell values. Also, the estrogen receptor positive cells had this change in levels of L-FABP, but no change was observed in few estrogen receptor negative cells that were tested as shown in FIG. 1.

Intestine-FABP:

The expression of Intestine-FABP was also shown to be upregulated in breast cancer cells compared to the normal breast cells. There was a 4–6 fold increase in the level of I-FABP when compared to the normal cells as shown in FIG. 2.

Adipose-FABP: Adipose-FABP is same as the MDGI (mammary derived growth inhibitor) and the expression of this FABP is downregulated in cancer cells. The normal levels of Adipose-FABP is downregulated by 5–6 fold in cancer cells as shown in FIG. 3.

CRAB-1: The levels of cellular retinoic acid binding protein expression remains the same in cancer and normal cells. The level of this FABP does not change with the stage of cancer as shown in FIG. 4.

Data from Prostate Cells:

Liver-FABP: In prostate cells only DU-145 cells expressed Liver-FABP, all other cells were negative for L-FABP. There was a 10 fold difference in normal versus DU-145 cells in expression of L-FABP as shown in FIG. 5.

Intestine-FABP: The normal cells expressed very low levels of I-FABP. There was a 4–6 fold increase in expression of I-FABP in LNCAP cells which are prostate cancer cells as shown in FIG. 6.

Adipose-FABP: The expression levels of Adipose-FABP was much higher in normal prostate cells when compared to the LNCAP cells. There was a five-fold decrease in the expression of Adipose-FABP in cancer cells as shown in FIG. 8.

Muscle-FABP: The level of Muscle-FABP was high in normal cells when compared to the cancer cells. The difference in levels was 4–6 fold as shown in FIG. 7.

CRAB-1: The levels of CRAB-1 expression did not change in normal and cancer prostate cells as shown in FIG. 9.

Using Human tissue samples we confirmed these findings for FABP changes in normal and two tumor samples from prostate cancer patients.

Peptides:

Specific peptides for these FABPs have been developed that will bind to the m-RNA of only one FABP and will not interact with the others. The specific peptides are designed to accomplish the inhibition of expression of the specific m-RNA genes. We will also design peptides representing unique regions of each specific FABP. We will synthesize these peptides, attach them to a carrier molecule and generate specific antibodies for each of FABPs. These antibodies are crucial for use in development of ELISA procedures to detect each of the specific FABPs in body fluids and, perhaps, to also use them for therapeutic interventions.

Oligos:

We have also designed specific Oligonucleotides that will recognize only the respective specific gene. These Oligos will be used for first quantitation of genes by using them as probes. Also we will make antisense RNA for these FABP genes which will be able to block the expression of Liver and Intestine-FABPs which we have shown to be upregulated in cancer cells.

The invention demonstrates in prostate and breast cancer cells that, there exist a balance of the good type of FABPs (A-FABP, E-FABP and Mus-FABP) and the bad type of FABPs (L-FABP, I-FABP and B-FABP). Change in this balance allows prediction of the stage of the cancer. Upon manipulation of the protein levels, by use of the drug HPA-Na, concomitant increasing A-FABP (FIG. 10), along with decreasing I-FABP (FIG. 11) proliferation of these cancer cells is blocked and they are forced towards a normal cell FABP profile.

Expression of different FABPs show a different pattern in cancer cells. High levels of Liver-FABP 10–15 fold correlates with aggressive stage of cancer in both prostate and breast cancer cells. In the case of breast cancer, all the cancer cell lines that we have tested to date show high levels of expression of L-FABP (virtually absent in normal cells) (FIG. 1); in contrast, our preliminary data suggests that I-FABP expression is related to stage or aggressiveness of the breast cancer (FIG. 2).

Upregulation of Intestine-FABP by 4–6 fold also correlates with cancerous stage. Most importantly, down regulation of Adipose or Muscle-FABP also suggests the onset of cancerous stage in both breast and prostate cancer cells (FIGS. 3, 7 and 8). Total disappearance of these FABPs is thought to be correlated with an advanced stage of cancer. This has been now confirmed with human tissue samples, which show a decrease in A-FABP and E-FABP and increase of B-FABP in prostate tumor samples.

While the preferred embodiments of the invention have been illustrated and described, it will be appreciated that various changes can be made therein without departing from the spirit and scope of the invention.

Tables 1 and 2 Show the Effective Concentration of HPA in Breast Cancer Cells:

Tables 1 and 2 show the concentrations required for $IC_{50}$ inhibition in cultures of wild type and multi-drug resistant MCF-7 human breast cancer cells, respectively. These tables show polyoxotungstates used on MCF-7 proliferation assay.

Table 3:
List of normal and tumor cell cultures used in these studies.

TABLE 1

| Name of polyoxotungstate[a] | $IC_{50}$ (Exp. 1) | $IC_{50}$ (Exp. #2) |
| --- | --- | --- |
| $K_{12.5}Na_{1.5}[NaP_5W_{30}O_{110}] \cdot nH_2O$ | 3.8 | 3.5 |
| $K_{13}[CaP_5W_{30}O_{110}] \cdot nH_2O$ | 4.5 | 5.0 |
| $K_{12}[BiP_5W_{30}O_{110}] \cdot nH_2O$ | N/A | 5.0 |
| $K_{12}[CeP_5W_{30}O_{110}] \cdot nH_2O$ | 4.3 | 5.0 |
| $K_{12}[SmP_5W_{30}O_{110}] \cdot nH_2O$ | 0.5 | 2.5 |
| $K_{12}[EuP_5W_{30}O_{110}] \cdot nH_2O$ | N/A | 4.5 |
| $K_{12}[GdP_5W_{30}O_{110}] \cdot nH_2O$ | 2.0 | 8.0 |
| $K_{12}[TbP_5W_{30}O_{110}] \cdot nH_2O$ | 1.0 | 8.0 |
| $K_{12}[DyP_5W_{30}O_{110}] \cdot nH_2O$ | 4.3 | 5.0 |
| $K_{12}[HoP_5W_{30}O_{110}] \cdot nH_2O$ | 3.0 | 4.5 |
| $K_{12}[ErP_5W_{30}O_{110}] \cdot nH_2O$ | 4.3 | 6.0 |
| $K_{12}[TmP_5W_{30}O_{110}] \cdot nH_2O$ | 0.25 | 10 |
| $K_{12}[YbP_5W_{30}O_{110}] \cdot nH_2O$ | 3.8 | 3.7 |
| $K_{12}[LuP_5W_{30}O_{110}] \cdot nH_2O$ | 1.0 | 5.0 |
| $K_{12}[UP_5W_{30}O_{110}] \cdot nH_2O$ | 1.0 | 10 |

$IC_{50}$ of WT MCF-7 breast cancer cells using polyoxotungstates. concentrations shown in µM
[a] n ranges from 20 to 30

TABLE 2

| Name of polyoxotungstate[a] | $IC_{50}$ (Exp. 1) | $IC_{50}$ (Exp. #2) |
| --- | --- | --- |
| $K_{12.5}Na_{1.5}[NaP_5W_{30}O_{110}] \cdot nH_2O$ | N/A | 2.1 |
| $K_{13}[CaP_5W_{30}O_{110}] \cdot nH_2O$ | 3.8 | 6.8 |
| $K_{12}[BiP_5W_{30}O_{110}] \cdot nH_2O$ | 3.0 | 2.5 |
| $K_{12}[CeP_5W_{30}O_{110}] \cdot nH_2O$ | 3.8 | 3.0 |
| $K_{12}[SmP_5W_{30}O_{110}] \cdot nH_2O$ | 3.8 | 4.1 |
| $K_{12}[EuP_5W_{30}O_{110}] \cdot nH_2O$ | 0.25 | 3.8 |
| $K_{12}[GdP_5W_{30}O_{110}] \cdot nH_2O$ | 4.3 | 4.6 |
| $K_{12}[TbP_5W_{30}O_{110}] \cdot nH_2O$ | 3.5 | 4.9 |
| $K_{12}[DyP_5W_{30}O_{110}] \cdot nH_2O$ | 3.8 | 2.3 |
| $K_{12}[HoP_5W_{30}O_{110}] \cdot nH_2O$ | 0.25 | 4.0 |
| $K_{12}[ErP_5W_{30}O_{110}] \cdot nH_2O$ | 4.0 | 1.0 |
| $K_{12}[TmP_5W_{30}O_{110}] \cdot nH_2O$ | 4.0 | 6.0 |
| $K_{12}[YbP_5W_{30}O_{110}] \cdot nH_2O$ | 5.0 | 6.3 |
| $K_{12}[LuP_5W_{30}O_{110}] \cdot nH_2O$ | 4.5 | 5.5 |
| $K_{12}[UP_5W_{30}O_{110}] \cdot nH_2O$ | 5.8 | 4.8 |

$IC_{50}$ of ADR MCF-7 breast cancer cells using polyoxotungstates. concentrations shown in µM
[a] n ranges from 20 to 30

TABLE 3

Prostate Cells:

Normal:

PrEC: Prostate normal primary cells obtained from Clonetics.
HPV-7: normal immortalized cells obtained from ATCC
Cancer:

PC-3: adenocarcinoma from bone metastasis from 62 yr old male, obtained from ATCC
DU 145: carcinoma of prostate from brain metastasis from 69 yr old male, obtained from ATCC
LNCAP: carcinoma of prostate from lymph node metastasis from 50 yr old male, obtained from ATCC.

Breast Cells:

Normal:

N-76 normal breast cells obtained as a gift from Vimala Band, MA.
Cancer:

MCF-7: breast carcinoma from ATCC.
T47D: breast carcinoma, obtained from ATCC.
MDA-MB-231, HS 578T also obtained from ATCC.
RNA obtained from NCI, NIH.
Lung NCI-H23, NCI-H226, NCI-H322, NCI-H460, NCI-H522, A549, HOP-62. HOP-92, EKVX
Ovary OVCAR-3, OVCAR-4, OVCAR-5, OVCAR-8, IGROV1, SK-OV-3
Melanoma LOX IMV1, MALME-3M, SK-MEL-2, SK-MEL-5, SK-MEL-28, UACC-62, UACC-257, M14
Kidney

UO-31, SN12C, A498, CAKI-1, RXF 393, ACHN, 786-0, TK-10
CNS

SNB-19, SNB-75, SF-268, SF-295, SF539, U251
Colon

HT-29, HCC-2998, HCT-116, SW-620, COLO 205, HCT-15, KM12
Leukemia

CCRF-CEM, K562, MOLT-4, HL-60, RPMI-8226, SR

What is claimed is:
1. A method of diagnosing breast cancer comprising the steps of:
   a) obtaining a tissue sample from a subject;

b) subjecting the sample to a detection method for measuring levels of fatty acid binding proteins (FABPs), said FABPs comprising Liver-FABP, Intestine-FABP, Adipose-FABP, Epidermal-FABP, and Heart/Muscle FABP;
c) detecting an amount of said FABP present in said sample of said subject;
d) comparing the amounts of expression of FABP in the sample to the amounts of expression of FABP in a non-cancerous control; and
e) diagnosing a presence of breast cancer by observing if the amounts of expression of the FABP in the sample show that Liver-FABP is up, Intestine-FABP is up, Adipose-FABP is down, Epidermal-FABP is down, and Heart/Muscle-FABP is down.

2. A method of diagnosing breast cancer comprising the steps of:
a) obtaining a tissue sample from a subject;
b) subjecting the sample to a detection method for measuring levels of FABP mRNA comprising Liver-FABP mRNA, Intestine-FABP mRNA, Adipose-FABP mRNA, Epidermal-FABP mRNA, and Heart/Muscle FABP mRNA;
c) detecting an amount of said FABP mRNA present in said sample of said subject;
d) comparing the amounts of FABP mRNA in the sample to the amounts of FABP mRNA in a non-cancerous control; and
e) diagnosing a presence of breast cancer by observing if the amounts Liver-FABP mRNA is up, Intestine-FABP mRNA is up, Adipose-FABP mRNA is down, Epidermal-FABP mRNA is down, and Heart/Muscle-FABP mRNA is down.

3. The method of claim 2, wherein the detection method for measuring levels of mRNA is RT-PCR.

4. A method of diagnosing prostate cancer comprising the steps of:
a) obtaining a tissue sample from a subject;
b) subjecting the sample to a detection method for measuring levels of FABPs, said FABPs comprising Liver-FABP, Intestine-FABP, Brain-FABP, Adipose-FABP, Epidermal-FABP, and Heart/Muscle FABP;
c) detecting an amount of said FABPs present in said sample of said subject;
d) comparing the amounts of FABPs in the sample to the amounts of expression of FABPs in a non-cancerous control; and
e) diagnosing a presence of prostate cancer if Liver-FABP is up, Intestine-FABP is up, Brain-FABP is up, Adipose-FABP is down, Epidermal-FABP is down, and Heart/Muscle-FABP is down.

5. The method claim 4, wherein the tissue sample is obtained from a patient that has undergone at least one of a PSA test and digital rectal examination.

6. A method of diagnosing prostate cancer comprising the steps of:
a) obtaining a tissue sample from a subject;
b) subjecting the sample to a detection method for measuring levels of FABP mRNA said FABP mRNA comprising Liver-FABP mRNA, Intestine-FABP mRNA, Adipose-FABP mRNA, Epidermal-FABP mRNA, Brain-FABP mRNA, and Heart/Muscle FABP mRNA;
c) detecting an amount of said FABP mRNA present in said sample of said subject;
d) comparing the amounts of FABP mRNA in the sample to the amounts of FABP mRNA in a non-cancerous control; and e) diagnosing a presence of prostate cancer if the amounts Liver-FABP mRNA is up, Intestine-FABP mRNA is up, Adipose-FABP mRNA is down, Epidermal-FABP mRNA is down, Brain-FABP mRNA is up, and Heart/Muscle-FABP mRNA is down.

7. The method of claim 6, wherein the detection method for measuring levels of mRNA is RT-PCR.

8. A method of diagnosing breast cancer comprising the steps of:
a) obtaining a tissue sample from a subject;
b) subjecting the sample to a detection method for measuring levels of FABPs;
c) detecting an amount of said FABP present in said sample of said subject;
d) comparing the amounts of expression of FABP in the sample to the amounts of expression of FABP in a non-cancerous control; and
e) diagnosing a presence of breast cancer by observing if the amounts of expression of FABP in the sample show that at least two have occurred selected from the group consisting of: Liver-FABP is up, Intestine-FABP is up, Adipose-FABP is down, and Heart/Muscle-FABP is down.

9. A method of diagnosing prostate cancer comprising the steps of:
a) obtaining a tissue sample from a subject;
b) subjecting the sample to a detection method for measuring levels of FABPs;
c) detecting an amount of said FABPs present in said sample of said subject;
d) comparing the amounts of expression of FABPs in the sample to the amounts of expression of FABPs in a non-cancerous control; and
e) diagnosing a presence of prostate cancer by observing if the amounts of expression of FABP in the sample show that at least two have occurred selected from the group consisting of: Liver-FABP is up, Intestine-FABP is up, Brain-FABP is up, Adipose-FABP is down, and Heart/Muscle-FABP is down.

10. A method of diagnosing breast cancer comprising:
a) obtaining a sample from said subject;
b) subjecting the sample to a detection method for measuring levels of Liver-FABP and Intestine-FABP;
c) detecting an amount of said fatty acid binding proteins (FABP's) in said sample of said subject;
d) comparing the amounts of said FABP's in the sample to the amounts of expression of FABP's in a non-cancerous control; and
e) diagnosing a presence of breast cancer if Liver-FABP is up and Intestine-FABP is up.

11. A method of diagnosing prostate cancer comprising:
a) obtaining a tissue sample from said subject;
b) subjecting the sample to a detection method for measuring levels of Liver-FABP, Brain-FABP and intestine-FABP;
c) detecting an amount of said FABP's in said sample of said subject;
d) comparing the amounts of said FABP's in the sample to the amount of expression of FABP's in a non-cancerous control; and
e) diagnosing a presence of prostate cancer if Liver-FABP is up, Brain-FABP is up and intestine-FABP is up.

* * * * *